(12) United States Patent
Voit et al.

(10) Patent No.: US 11,693,013 B2
(45) Date of Patent: Jul. 4, 2023

(54) METHOD RELATING TO MYOSTATIN PATHWAY INHIBITION

(71) Applicant: UCL Business Ltd., London (GB)

(72) Inventors: Thomas Voit, London (GB); Julie Dumonceaux, London (GB); Virginie Mariot, London (GB)

(73) Assignee: UCL Business Ltd., London (GB)

( * ) Notice: Subject to any disclaimer, the term of this patent is extended or adjusted under 35 U.S.C. 154(b) by 164 days.

(21) Appl. No.: 16/492,590

(22) PCT Filed: Mar. 12, 2018

(86) PCT No.: PCT/GB2018/050619
§ 371 (c)(1),
(2) Date: Sep. 9, 2019

(87) PCT Pub. No.: WO2018/162931
PCT Pub. Date: Sep. 13, 2018

(65) Prior Publication Data
US 2021/0140976 A1    May 13, 2021

(30) Foreign Application Priority Data

Mar. 10, 2017 (GB) ..................................... 1703869
Aug. 24, 2017 (GB) ..................................... 1713597

(51) Int. Cl.
*G01N 33/68* (2006.01)
*A61K 38/17* (2006.01)
*G01N 33/74* (2006.01)

(52) U.S. Cl.
CPC ....... *G01N 33/6887* (2013.01); *A61K 38/177* (2013.01); *G01N 33/74* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,888,012 B2* | 2/2011 | Iversen | ................... | A61P 21/00 435/6.16 |
| 2008/0299126 A1* | 12/2008 | Han | ....................... | A61P 13/12 424/139.1 |
| 2010/0272734 A1 | 10/2010 | Catrin et al. | | |
| 2011/0166082 A1 | 7/2011 | Iverson et al. | | |
| 2015/0152194 A1* | 6/2015 | Han | ................... | C07K 16/2863 424/136.1 |

FOREIGN PATENT DOCUMENTS

| WO | WO 2006/086667 A2 | 8/2006 |
|---|---|---|
| WO | WO 2008/036127 A2 | 3/2008 |
| WO | WO 2013/142816 A1 | 9/2013 |

OTHER PUBLICATIONS

Verzola et al. (2011, Kidney International 79:773-782).*
Yano et al. (2015, PLoS ONE 10(10):e0141035; pp. 1-9).*
Avin et al. (Aug. 2016, PLoS ONE 11 (8):e0159411, pp. 1-15).*
Gonzalez-Cadavid et al. (1998, PNAS USA 95(25):14938-14943).*
Awano et al., "Wide ranges of serum myostatin concentrations in Dechenne muscular dystrophy patients," *Clinica Chiminca Acta.* 391(1-2): 115-117 (2008).
Cohen et al., "Muscle wasting in disease: molecular mechanisms and promising therapies," *Nature Reviews Drug Discovery* 14(1):58-74 (Dec. 31, 2017).
Dumonceaux et al., "Combination of myostatin pathway interference and dystrophin rescue enhances tetanic and specific force in dystrophic mdx mice," *Molecular Therapy* 18(5): 881-887 (May 2010).
Feng et al., "Pharmacologically induced mouse model of adult spinal muscular atrophy to evaluate effectiveness of therapeutics after disease onset," *Human Molecular Genetics* 25(5): 964-975 (Jan. 2016).
Search and Examination Report from Great Britain Application No. GB 1703869.3, 8 pages (dated Dec. 27, 2017).
Mariot et al., "Downregulation of myostatin pathway in neuromuscular diseases may explain challenges of anti-myostatin therapeutic approaches," *Nature Communications* 8(1):1859, 8 pages (Nov. 30, 2017).
Rodino-Klapac et al., "Micro-dystrophin and follistatin co-delivery restores muscle function in aged DMD model," *Human Molecular Genetics* 22(24): 4929-4937 (2013).
Smith and Lin, "Myostatin inhibitors as therapies for muscle wasting associates with cancer and other disorders," *Current Opinion Support Palliative Care* 7(4): 352-360 (Dec. 2013).
Wagner et al., "A phase I/II trial of MYO-029 in adult subjects with muscular dystrophy," *Annuals of Neurology* 63: 561-571 (2008).
Cohen et al., "Muscle wasting in disease: molecular mechanisms and promising therapies," *Nature Reviews Drug Discovery* 14(1):58-74 (Dec. 31, 2017)(Abstract).
International Search Report and Written Opinion from parent PCT Application No. PCT/GB2018/050619, 21 pages (dated Jul. 26, 2018).
Anaya-Segura et al., "Non-Invasive Biomarkers for Duchenne Muscular Dystrophy and Carrier Detection," *Molecules* 20: 11154-11172 (2015).

(Continued)

*Primary Examiner* — Elizabeth C. Kemmerer
(74) *Attorney, Agent, or Firm* — Klarquist Sparkman, LLP

(57) ABSTRACT

The present invention provides a method for determining whether a patient will respond to treatment with a myostatin pathway inhibitor, the method comprising: (a) determining a level of myostatin and/or activin type II receptor (ActRII) and/or follistatin in at least one muscle biopsy obtained from a treatment target muscle in a subject having or suspected of having muscle atrophy or a muscle wasting condition; and (b) determining a level of myostatin and/or follistatin in a systemic sample obtained from the patient, wherein if: (i) the level of myostatin in the systemic sample is higher than a threshold and/or if the level of follistatin in the sample is lower than a threshold; and (ii) the level of myostatin and/or ActRII receptor in the at least one biopsy sample is higher than a threshold level and/or if the level of follistatin in the at least one biopsy sample is lower than a threshold level, the patient will respond to treatment.

76 Claims, 5 Drawing Sheets

Figure 1:
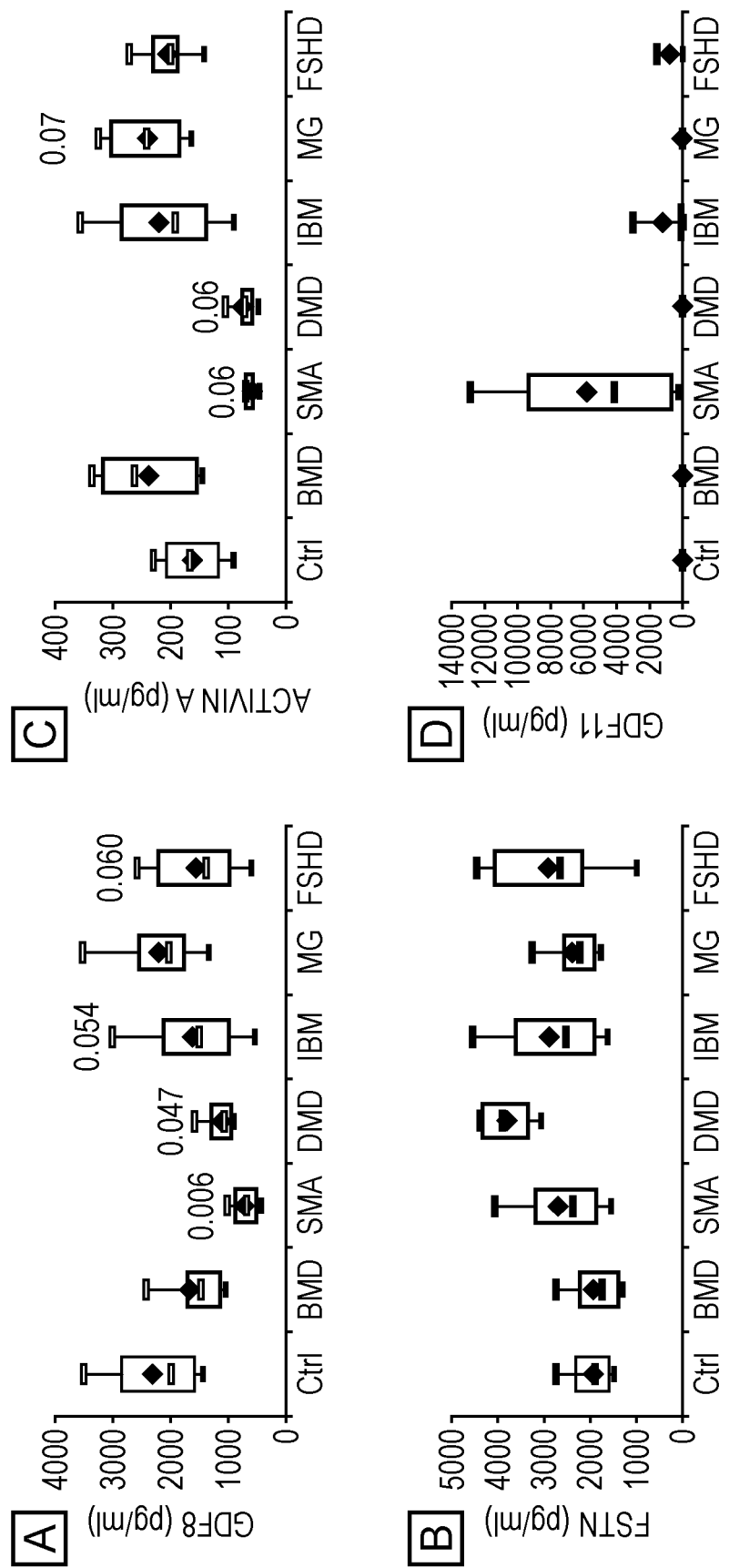

Specification includes a Sequence Listing.

(56) References Cited

OTHER PUBLICATIONS

Hammers et al., "Supraphysiological levels of GDF11 induce striated muscle atrophy," *EMBO Molecular Medicine* 9(4): 531-544 (2017).
Search and Examination Report from Great Britain Application No. GB1713597.1, 4 pages (dated Jun. 18, 2018).

* cited by examiner

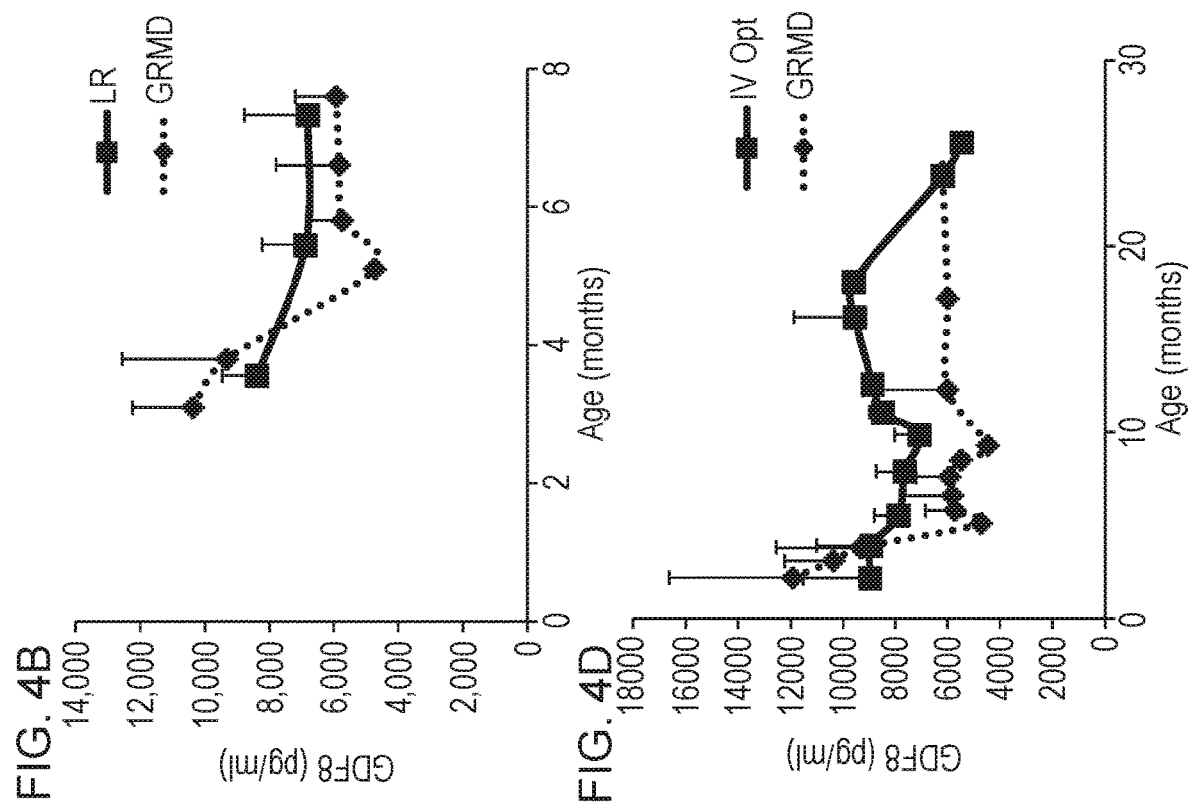
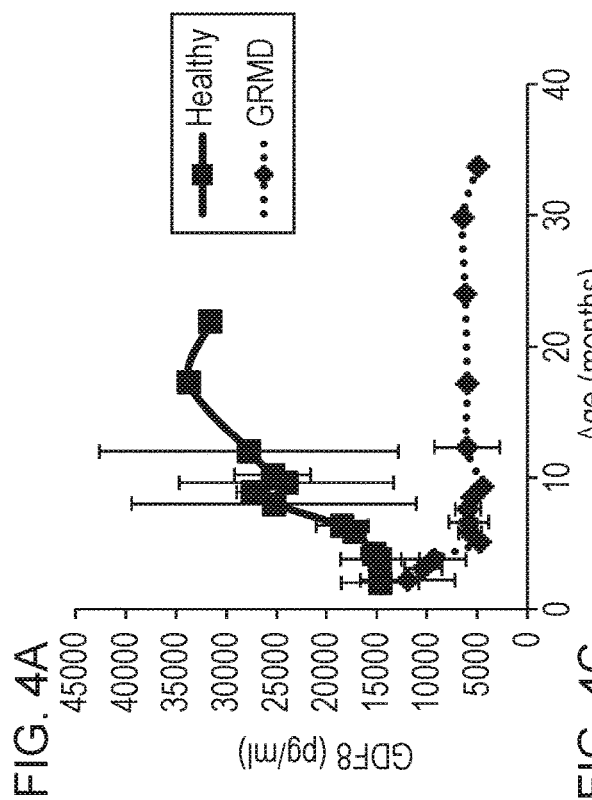
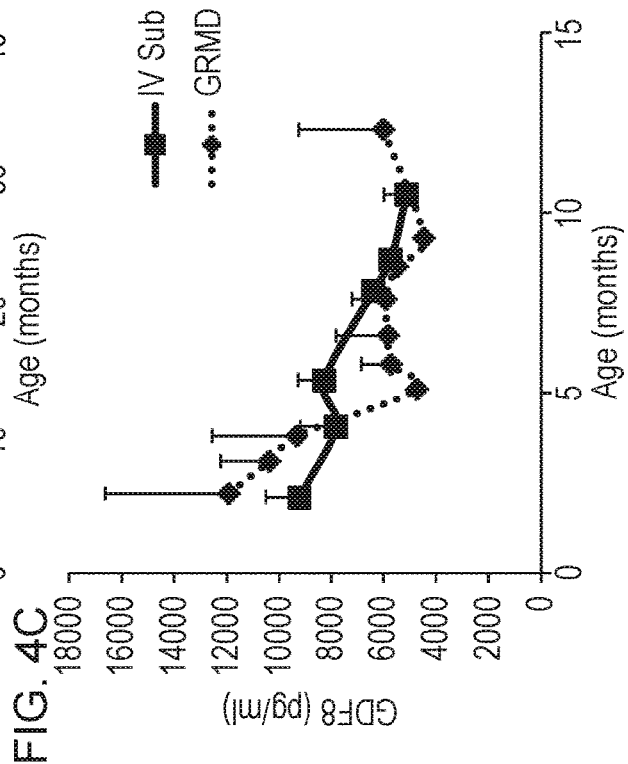

SEQUENCE LISTING

```
<160> NUMBER OF SEQ ID NOS: 42

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ctggctccta gcaccatgaa                                                     20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
ctgcttgctg atccacatct                                                     20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ccttcattgg aaacagcaca                                                     20

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cctcctctcc gaaatcctct                                                     20

<210> SEQ ID NO 5
```

```
<211> LENGTH: 20
<212> TYPE: DNA
<213> ORGANISM: Artificial Sequence
<220> FEATURE:
<223> OTHER INFORMATION: Primer

<400> SEQUENCE: 5
ttgtgatggg tgtgaaccac                                                 20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ttcagctctg ggatgacctt                                                 20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcaaactttg ctttccctgg                                                 20

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
acttcgagag gtccttttca cc                                              22

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctccaagcag atgcagcaga                                                 20

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
atagccttgc gcatcatgg                                                  19

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
```
gctcagctca tgaacgact                                                19

<210> SEQ ID NO 12
<211> LENGTH: 19
<212> TYPE: DNA
<213> ORGANISM: Artificial Sequence
<220> FEATURE:
<223> OTHER INFORMATION: Primer

<400> SEQUENCE: 12
ctctgccacg actgcttgt                                                19

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
ctcttcaagt ggatgatttt c                                             21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
acagtaggca ttattggtct g                                             21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gcactggtat ttggcagagt a                                             21

<210> SEQ ID NO 16
<211> LENGTH: 21
<212> TYPE: DNA
<213> ORGANISM: Artificial Sequence
<220> FEATURE:
<223> OTHER INFORMATION: Primer

<400> SEQUENCE: 16
cacactctcc tgagcagtaa t                                             21

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctctctttct ggcctggagg                                               20

<210> SEQ ID NO 18
<211> LENGTH: 22
<212> TYPE: DNA

```
<213> ORGANISM: Artificial Sequence
<220> FEATURE:
<223> OTHER INFORMATION: Primer

<400> SEQUENCE: 18
tgctggatga cgtgagtaaa cc                                              22

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
aaggtgaagg tcggagtcaa cgg                                             23

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tgacaagctt cccgttctca gcc                                             23

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
ctcatttgga attttgccga tt                                              22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ccgagtgaag atcccctttt ta                                              22

<210> SEQ ID NO 23
<211> LENGTH: 22
<212> TYPE: DNA
<213> ORGANISM: Artificial Sequence
<220> FEATURE:
<223> OTHER INFORMATION: Primer

<400> SEQUENCE: 23
tccaggcttt aggtatcacc ac                                              22

<210> SEQ ID NO 24
<211> LENGTH: 21
<212> TYPE: DNA
<213> ORGANISM: Artificial Sequence
<220> FEATURE:
<223> OTHER INFORMATION: Primer

<400> SEQUENCE: 24
gctcccactt tgtctccagt c                                               21
```

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cctaaagcat acgggtcctg                                               20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tttcactttg ccaaacacca                                               20

<210> SEQ ID NO 27
<211> LENGTH: 19
<212> TYPE: DNA
<213> ORGANISM: Artificial Sequence
<220> FEATURE:
<223> OTHER INFORMATION: Primer

<400> SEQUENCE: 27
ctcctctggg gatcgctgt                                                19

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ctcccagttg gcgttgtagt                                               20

<210> SEQ ID NO 29
<211> LENGTH: 17
<212> TYPE: DNA
<213> ORGANISM: Artificial Sequence
<220> FEATURE:
<223> OTHER INFORMATION: Primer

<400> SEQUENCE: 29
cggctgagca cctcgtg                                                  17

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
ttcttgttca ttcggcattt                                               20

<210> SEQ ID NO 31
<211> LENGTH: 20
<212> TYPE: DNA
<213> ORGANISM: Artificial Sequence
<220> FEATURE:

```
<223> OTHER INFORMATION: Primer

<400> SEQUENCE: 31
ttttacccaa agctcctcca                                               20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gagtctcgac gggtctcaaa                                               20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
cacacttctg cacgctccac                                               20

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
tttgccgagt caggcacag                                                19

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
atcagccggg aggtagtgaa                                               20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
ctgggccatg cttatgaccg t                                             21

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ttatggagca gacctcggag                                               20
```

```
<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
aaatctcgaa gtgcagcgtc                                              20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
attggcagag catcgacttc                                              20

<210> SEQ ID NO 40
<211> LENGTH: 21
<212> TYPE: DNA
<213> ORGANISM: Artificial Sequence
<220> FEATURE:
<223> OTHER INFORMATION: Primer

<400> SEQUENCE: 40
ttttgtgttc tctaggactc g                                            21

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gcaatgaaga gctgaatgcc a                                            21

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
tgtcaaagac acgcagaccc t                                            21
```

METHOD RELATING TO MYOSTATIN PATHWAY INHIBITION

CROSS REFERENCE TO RELATED APPLICATION

This is a § 371 U.S. national stage of International Application No. PCT/GB2018/050619, filed Mar. 12, 2018, and which claims the benefit of Great Britain Patent Application No. 1703869.6, filed on Mar. 10, 2017, and Great Britain Patent Application No. 1713597.1, filed on Aug. 24, 2017.

SEQUENCE LISTING

The Sequence Listing is submitted as an ASCII text file [8050-103241-01_Sequence_Listing.txt, Sep. 10, 2019, 7.73 KB], which is incorporated by reference herein.

The present invention relates to methods for determining whether a patient will respond to a myostatin pathway inhibitor, methods for treating muscle atrophy or muscle wasting conditions and methods for monitoring such treatment.

Skeletal muscle mass is controlled by different pathways among them the myostatin pathway. Myostatin, also known as Growth Differentiation Factor-8 (GDF-8), is a member of the transforming growth factor-beta (TGF-beta) family of proteins whose function appears to be conserved across species. Because several spontaneous mutations in the myostatin gene have been correlated with muscle hypertrophy in animals or even in man, myostatin inhibition had been seen as a promising tool to fight muscle atrophy in different diseases including muscle diseases.

Myostatin is a secreted protein, synthetized by skeletal muscle as a precursor, which undergoes maturation steps. Several myostatin inhibitory drugs have been designed targeting different stages of the myostatin biosynthesis or pathway including (i) monoclonal antibodies targeting myostatin, (ii) monoclonal antibodies targeting myostatin's receptor, activin type II receptor (ActRII), (iii) ActRII decoys, and (iv) follistatin overexpression, which functions as a myostatin antagonist by preventing receptor binding (for review see Cohen et al., 2015). During the last 15 years, at least 6 molecules (MYO-029, BMS-986089, PF-14 06252616, ACE-083/-031, BYM338, FS-344) have been developed by pharmaceutical companies to block myostatin pathways (https://clinicaltrials.gov). These molecules are/were evaluated in several neuromuscular diseases that show muscular wasting or atrophy but so far the published results have been largely disappointing. Significant improvements in muscle strength or physical function have not been reached, with the exception of one phase 2 trial using an AAV vector encoding the follistatin isoform FS344 intramuscularly injected in Becker Muscular Dystrophy (BMD) patients. Several explanations have been proposed, among them the specificity of the drugs themselves and the possibility that they do not target the correct form of myostatin or do not target other growth factors besides myostatin implicated in muscle mass regulation. However, in animals, several laboratories have demonstrated that myostatin pathway inhibition leads to muscle hypertrophy and enhances tetanic force in controls or in several murine models of muscle diseases such as the mdx mouse, a murine model for Duchenne Muscular Dystrophy (DMD).

Some attempts have been made to improve the clinical efficacy of anti-myostatin treatment. For example, US2011/0166082 describes a method for treating skeletal muscle mass deficiency and proposes a method comprising (i) measuring the circulating levels of myostatin in patients before anti-myostatin injection and (ii) if this level is above a selected threshold level for normal average individuals (typically more than 10-20%) or (iii) if the patient presents obvious muscle wasting, then the patient is a candidate for anti-myostatin administration. US2011/0166082 therefore teaches that patients presenting with obvious muscle wasting or with myostatin levels above that of normal average individuals are candidates for an anti-myostatin approach.

The present inventors have recognised that the poor clinical efficacy of anti-myostatin molecules in several of the human studies to date was due to the surprising fact that the expression level of the targeted protein itself was reduced, and/or the level of ActRII strongly decreased. Indeed, a treatment targeting circulating myostatin is unlikely to work if the level of circulating myostatin is already very low in patients. Similarly, activated myostatin C-peptide cannot transmit its signalling to the muscle fibre if insufficient ActRII is expressed. A combination of both limiting conditions—a further surprising finding—additionally potentiates the refractory state of skeletal muscle to a myostatin inhibition approach. The present inventors have analyzed the expression levels of different actors of the myostatin network at mRNA and/or protein levels in the sera and/or biopsies of patients with different muscular diseases and in a mouse model of the congenital myotubular myopathy, and in a dog model of Duchenne muscular dystrophy, all of which have an underlying muscle wasting/atrophying process in common. The inventors have determined that in several neuromuscular diseases the myostatin pathway is shut down at mRNA level in muscle biopsies, leading to low levels of circulating and endogenous muscle myostatin and high levels of follistatin. This regulation of the myostatin network is disease-dependent, with the patients affected by the most atrophying disease showing the strongest extinction of the myostatin pathway. Importantly, decreased myostatin synthesis is frequently accompanied by down-regulation of the muscle ActRII, thereby further down-regulating the myostatin pathway. Further inhibition of this pathway by an exogenous compound (such as a monoclonal antibody or vector-mediated inhibition) in the presence of strong down regulation in severely affected muscles may not be an efficient strategy to increase muscle mass. However, the inventors have surprisingly found that this blockage is reversible upon proper treatment of the primary cause of the disease, as exemplified with the myotubular myopathy model described later in this specification.

Accordingly, in a first aspect the present invention provides a method for determining whether a patient will respond to treatment with a myostatin pathway inhibitor, the method comprising: (a) determining a level of myostatin and/or activin type II receptor (ActRII) and/or follistatin in at least one muscle biopsy obtained from a treatment target muscle in a subject having or suspected of having muscle atrophy or a muscle wasting condition; and (b) determining a level of myostatin and/or follistatin in a systemic sample obtained from the patient, wherein if: (i) the level of myostatin in the systemic sample is higher than a threshold and/or if the level of follistatin in the sample is lower than a threshold; and (ii) the level of myostatin and/or ActRII receptor in the at least one biopsy sample is higher than a threshold level and/or if the level of follistatin in the at least one biopsy sample is lower than a threshold level, the patient will respond to treatment.

Additionally or alternatively, the method may comprise determining levels of activin A in the muscle biopsy and systemic samples, wherein if the level of activin A is higher than threshold levels for each sample, the patient will respond to treatment with a myostatin and/or activin A pathway inhibitor. Like myostatin, activin A binds to the ActRII receptor and activates Smad2/3 signalling. Activin A is now known to suppress muscle growth in a similar way to myostatin (Latres et al 2017), and indeed, has been described as a more potent regulator of muscle mass in primates than myostatin. Activin A levels are indicative of myostatin levels and can therefore provide an indication of whether a subject is likely to respond to an anti-myostatin approach.

In the context of the present invention, systemic levels of myostatin and/or follistatin, and levels of follistatin, myostatin and/or ActRII as expressed in the muscle may be considered to be essential actors of the myostatin pathway. In the context of the present invention, due to its action on the ActRII receptor, activin A can be considered to be an essential actor of the downstream myostatin pathway.

Systemic levels of myostatin and/or follistatin and/or activin A provide an indication of the overall homeostasis of the skeletal muscle system, and consequently of the disease status of the patient affected by a muscle wasting or atrophying condition. If levels of circulating myostatin and/or activin A are too low and/or if levels of circulating follistatin are too high this may be an indication that a patient will not respond to treatment with a myostatin pathway inhibitor. However, an important feature of the present invention is the measurement of levels of myostatin and/or ActRII and/or follistatin and/or activin A in at least one muscle biopsy obtained from a treatment target muscle. The present inventors have determined that low circulating levels of myostatin are not necessarily indicative of net muscle loss. Indeed, in muscle atrophy or muscle wasting conditions it appears that the body automatically inhibits the myostatin pathway in order to try to stabilise the affected muscle(s). The muscle fibres may be present, but will be in a dormant state, unable to respond to a myostatin pathway inhibitor. However, depending on the specific muscle atrophy or muscle wasting condition, different muscles and/or different parts of particular muscles (i.e. different fascicles) may be affected. A key feature of the present invention therefore relates to determining levels of myostatin and/or ActRII and/or follistatin and/or activin A in at least one muscle biopsy obtained from a treatment target muscle. For example, if a medical practitioner is seeking to improve ambulation, key treatment target muscles will be weight-bearing muscles in the lower limbs. It is necessary to determine whether those specific muscle groups targeted by an anti-myostatin treatment approach are capable of responding to a myostatin pathway inhibitor, and merely measuring systemic levels of myostatin, activin A or follistatin would not be sufficient to make this determination. In summary: when treating neuromuscular patients, i.e., patients with muscle wasting, measuring both target tissue and serum myostatin gives a surprising result because, as myostatin is synthesized by muscle, it would have been expected that a decrease in circulating myostatin is a reflexion of the muscle wastage. However, the present inventors have demonstrated that this hypothesis is wrong, and a lower synthesis of myostatin was observed at mRNA level in the muscle biopsies.

The determination of a high or low level of myostatin, GDF11, activin A, follistatin or ActRII is based on a control/threshold level, which is typically determined from a relevant population of individuals with significant muscle atrophy and/or a severe or advanced muscle wasting condition by comparing them to a healthy, age- and gender matched control population. These individuals with a muscle wasting or atrophying condition have very low systemic and/or local levels of myostatin and/or ActRII and/or activin A and/or high systemic and/or local levels of follistatin, indicating that the myostatin pathway is suppressed and therefore incapable of responding to a myostatin pathway inhibitor. For example, when compared to an aged matched population without significant medical disorders the myostatin and/or ActRII and/or activin A levels of the population of individuals with significant muscle atrophy and/or severe or advanced muscle wasting condition may be 10% to 70% lower, or 20% to 50% lower, or 20% to 30% lower. The relevant population can be defined based on, for example, diet, lifestyle, age, ethnic background or any other characteristic that can affect the normal levels of the markers.

Once the control/threshold levels are known, the measured levels can be compared and the significance of the difference determined using standard statistical methods. If there is a substantial difference between the measured level and the control/threshold level (i.e. a statistically significant difference), then the individual from whom the levels have been measured may be considered to have unusual levels of the marker, those unusual levels being higher or lower than the control/threshold level determined from the relevant population of individuals with significant muscle atrophy and/or a severe or advanced muscle wasting condition. If the levels of myostatin and/or ActRII and/or activin A are statistically higher than the threshold level and/or if the levels of follistatin are statistically lower than the threshold level this is an indication that the myostatin pathway of the individual from whom the levels have been measured may be capable of responding to a myostatin and/or activin A pathway inhibitor.

A patient that is likely to respond to treatment will therefore have a higher level of myostatin and/or ActRII and/or activin A than a control/threshold level determined from a relevant population of individuals with significant muscle atrophy and/or a severe or advanced muscle wasting condition, but will also likely have a lower myostatin and/or ActRII and/or activin A level than a healthy, age- and gender matched control population.

Once a patient has been determined to have the capability to respond to treatment with a myostatin pathway inhibitor, the method may further comprise administering a myostatin or activin A pathway inhibitor to the patient.

The patient and/or subject is preferably a mammal, including a human, and may be of any age or a paediatric or a geriatric patient. In embodiments of the invention the patient may have or be suspected of having muscle atrophy or a muscle wasting condition.

The present invention also provides a method for treating muscle atrophy or a muscle wasting condition, the method comprising: (a) determining a level of myostatin and/or activin type II receptor (ActRII) and/or follistatin in at least one muscle biopsy obtained from a treatment target muscle in a subject having or suspected of having muscle atrophy or a muscle wasting condition; (b) determining a level of myostatin and/or follistatin in a systemic sample obtained from the patient; and if: (i) the level of myostatin in the systemic sample is higher than a threshold and/or if the level of follistatin in the sample is lower than a threshold; and (ii) the level of myostatin and/or ActRII receptor in the at least one biopsy sample is higher than a threshold level and/or if the level of follistatin in the at least one biopsy sample is lower than a threshold level, administering a myostatin pathway inhibitor to the patient.

Additionally or alternatively, the method may comprise determining levels of activin A in the muscle biopsy and systemic samples, wherein if the level of activin A is higher than threshold levels for each sample, administering a myostatin or activin A pathway inhibitor to the patient.

According to the methods of the present invention, the myostatin or activin A pathway inhibitor may be administered systemically or may be administered locally to one or more target muscles, such as skeletal muscles. Suitable routes of administration may include parenteral administration, such as intravenous, subcutaneous or intramuscular administration.

The myostatin or activin A pathway inhibitor may be administered in the form of a pharmaceutical composition, which may be sterile and may comprise one or more pharmaceutically acceptable carriers or excipients. Suitable carriers and excipients will be familiar to the skilled person and may be optimised in line with the intended route of delivery. For example, suitable pharmaceutical compositions may include buffers, binders, preservatives, thickeners or antioxidants.

Myostatin, follistatin, activin A, GDF11, and/or ActRII may be measured as protein or mRNA. Proteins and mRNA may be measured using methods that will be familiar to the person skilled in the art. For example, proteins may be identified by contacting the protein of interest with an appropriate antibody, which may comprise a label. Assay techniques such as ELISA or Western blot may be used. mRNA may be measured by techniques such as PCR, including qPCR or digital PCR, utilising primers specific to the target mRNA sequence of interest.

In an alternative embodiment, the present invention relates to evaluation of systemic GDF11 levels in patients having or suspected of having in spinal muscular atrophy (SMA). The systemic sample may be measured from a serum sample obtained from the patient. GDF11 is a known negative regulator of myogenesis (Gamer et al 2001). AAV-mediated gene delivery has been shown to inhibit skeletal muscle growth (Jin et al 2018) and supraphysiological administration of GDF11 has been shown to induce cachexia (Jones et al 2018). Because GDF11 is also known to act via the ActII receptor and thereby induce muscular atrophy, selective blockage of GDF11 in SMA may provide a useful approach to alleviate muscle atrophy in this condition.

As mentioned above, myostatin is synthesised by muscle fibres as an inactive precursor or pro-peptide, which is a 375 amino acid protein. The pro-peptide is proteolytically processed into a shorter, mature, active form by a protease, which cleaves the covalently bound NH2-terminal, or "pro-domain" portion of the protein, resulting in an active COOH-terminal dimer. The myostatin pro-peptide has two distinct functions in guiding protein folding and regulating biological activity of myostatin (through cleavage of the pro-domain). The mature form of the myostatin protein consists of two identical 109 amino acid residues. The mature form of myostatin binds to the ActII receptor to activate a downstream cell signalling cascade via Alk-3 or Alk-4, the signalling cascade including activation of transcription factors such as SMAD2 and SMAD3, which induce myostatin-specific gene expression. In embodiments of the invention myostatin may be measured in the pro-peptide form, i.e. as a latent complex (non-covalently bound to its pro-domain) or bound to other inhibitory proteins, such as follistatin. Preferably myostatin is measured in the mature protein form.

Muscle biopsies will be familiar to the person skilled in the art and may be obtained from any target muscle. In preferred embodiments of the invention the muscle biopsy is obtained from a skeletal muscle. The skeletal muscle is preferably the treatment target muscle of interest.

Suitable systemic samples include bodily fluid samples, such as a whole blood sample, a serum sample, a plasma sample or a urine sample.

The muscle atrophy or muscle wasting condition may be selected from a muscle dystrophy such as: Becker Muscular Dystrophy (BMD), Duchenne Muscular Dystrophy (DMD), Facioscapulohumeral Dystrophy (FSHD), Limb Girdle Muscular Dystrophy (LGMD), or Congenital Muscular Dystrophy (CMD); a central or spinal muscular atrophy such as: Amyotrophic Lateral Sclerosis (ALS) or Spinal Muscular Atrophy (SMA); a neurogenic muscular atrophy such as: Charcot-Marie-Tooth peripheral neuropathy; a congenital myopathy such as: Myotubular myopathy; an 'idiopathic' muscle wasting condition such as: Inclusion Body Myositis (IBM) or age-related sarcopenia.

The myostatin pathway inhibitor may be a myostatin antagonist or an ActRII antagonist. In embodiments of the invention the myostatin pathway inhibitor may be a myostatin inhibitor.

Suitable myostatin antagonists include anti-myostatin antibodies, myostatin decoys, follistatin, or follistatin analogues. Myostatin pathway inhibitors may also include abolishing or impeding the myostatin pathway through the use of siRNA, shRNA, antisense oligonucleotides, miRNA interference through gene silencing using exon skipping or nuclease-mediated invalidation through CRISPR or TALEN. Alternatively, the myostatin antagonist may be provided in the form of myostatin pro-peptide overexpression or altered myostatin pro-peptide expression, either or both of which may be delivered by gene therapy. Altered myostatin pro-peptide expression may comprise tighter binding of the pro-domain to the mature myostatin protein, thereby inhibiting cleavage of the pro-peptide into mature myostatin, and thereby inhibiting myostatin function.

Suitable ActRII antagonists include anti-ActRII antibodies, ActRII decoys or inhibitors of effectors downstream of the ActRII, as well as small molecules down-regulating myostatin. In embodiments of the invention, soluble ActRII may be administered to outcompete the receptor, acting as a decoy for the mature myostatin protein.

In embodiments of the invention the myostatin pathway inhibitor may be selected from one or more molecules known to block myostatin pathways including but not limited to PF06252616, FS344, Bimagrumab, ACE-083, ACE-031, ACE-2494, AAV1-FS344, AAV9-FS344, BMS-986089 or MYO-029.

GDF11 pathway inhibition may be achieved through anti-GDF11 antibodies or human IgG1 Fc-fused GDF11 propeptide.

In a further aspect the present invention provides a dystrophin or myotubularin (MTM1) gene or pathology correcting therapy and a myostatin pathway inhibitor for use in treating muscle atrophy or a muscle wasting condition.

As mentioned above, muscle atrophy or a muscle wasting condition will lead to muscle fibres becoming dormant, rendering them unable to respond to a myostatin pathway inhibitor. Surprisingly, the present inventors have found that this effect of muscle atrophy or a muscle wasting condition can be reversed utilising gene therapy or pathology correcting therapy. While not being directly associated with myostatin, MTM1 encodes a phosphatidylinositol-3-phosphatase and is required for muscle cell differentiation. Surprisingly, reinstating MTM1 gene expression leads to reactivation of myostatin synthesis by muscle fibres. The muscle is then able to respond to a myostatin pathway inhibitor and improvements in myogenesis, i.e. muscle cell growth and differentiation, alleviate or reverse the effects of the muscle atrophy or muscle wasting condition. Similar effects can be achieved by reinstating dystrophin gene expression. Dystrophin deficiency underlies the pathology of Duchenne and Becker muscular dystrophies and reinstating dystrophin gene expression can lead to reactivation of myostatin synthesis by muscle fibres, rendering them able to respond to a myostatin pathway inhibitor.

The muscle atrophy or a muscle wasting condition may be any genetically determined neuromuscular condition where a gene therapy, a cell therapy, or a small molecule therapy is capable of stopping or reverting the underlying pathogenic mechanism. All genetic muscle disorders listed above may be suitable for treatment.

Suitable myostatin pathway inhibitors and forms and routes of administration include those described above in relation to other aspects of the invention.

A pathology correcting therapy may include a cell or small molecule therapy capable of stopping or reversing the pathology underlying the muscle atrophy or muscle wasting condition. For example, a small molecule therapy may be used to provide an indirect gene therapy, acting by targeted promotor stimulation or splicing modification.

Gene therapy may be provided in the form of a recombinant viral vector supplying or partially or fully correcting a missing gene such as MTM1 or the dystrophin gene, or suppressing a damaging gene expression such as SOD-1 through RNA interference or out-of-frame exon skipping of the damaging gene. Suitable viral vectors will be familiar to the skilled person and include a retrovirus, an adenovirus, a lentivirus, herpes simplex virus, and adeno-associated virus. Other viral vectors are envisaged.

The gene or pathology correcting therapy and myostatin pathway inhibitor may be administered separately, simultaneously or sequentially. Preferably, the gene or pathology correcting therapy is administered prior to the myostatin pathway inhibitor. The gene or pathology correcting therapy may be administered at least two weeks, or at least three weeks, or at least four weeks prior to the myostatin pathway inhibitor. In embodiments of the invention the gene or pathology correcting therapy may be administered at least one month or at least two months or at least three months prior to the myostatin pathway inhibitor. The time period will be dependent on the underlying pathology and can be determined by a medical practitioner. Once the target muscle(s) are sufficiently healthy to start synthesising myostatin, the myostatin pathway inhibitor can be administered. Muscle biopsies and/or systemic samples as described above may be utilised to monitor levels of essential actors of the myostatin pathway in the target muscle(s).

The present invention also provides a method for improving or monitoring dystrophin or MTM1 gene or pathology correcting therapy, the method comprising determining a level of myostatin and/or ActRII and/or follistatin in a sample obtained from a subject.

Preferably the level of myostatin and/or follistatin is compared to a threshold as described above. Optionally, if the level of myostatin is below the threshold and/or if the level of follistatin is above the threshold, at least one further round of gene or pathology correcting therapy may be administered.

In a still further aspect, the present invention provides a dystrophin or MTM1 gene or pathology correcting therapy for use in treating muscle atrophy or a muscle wasting condition in a subject, wherein the subject is characterised by having a myostatin and/or ActRII level lower than a threshold level.

The subject may be characterised by having a systemic or local level of myostatin or ActRII that is lower than a threshold level. Threshold levels can be determined as described above. Suitable samples may be obtained and/or measured as described in relation to the aspects of the invention. In embodiments of the invention, the subject may be characterised by having at least one skeletal muscle that does not express ActRII at normal levels, said muscle being determined by at least one muscle biopsy indicating reduced levels of active ActRII.

The effect of myostatin on skeletal muscle is exclusively mediated by mature myostatin acting on ActRII. Consequently, if skeletal muscle expresses little or even no ActRII it cannot be 'sensitive' to the effects of mature myostatin on promoting muscle growth.

The present invention also provides a method for determining anabolic capacity of the skeletal muscle system of a subject, the method comprising: (a) determining a level of myostatin and/or follistatin in a systemic sample obtained from the subject; and/or (b) determining a level of myostatin and/or ActRII and/or follistatin in at least one skeletal muscle biopsy obtained from the subject; wherein if (i) the level of myostatin in the systemic sample is lower than a threshold and/or if the level of follistatin in the sample is higher than a threshold; and/or (ii) the level of myostatin and/or ActRII receptor in the at least one biopsy sample is lower than a threshold level and/or if the level of follistatin in the at least one biopsy sample is higher than a threshold level, the anabolic capacity of the skeletal muscle system is compromised, indicating the existence of a muscle wasting process in the subject. Threshold levels can be determined by comparison with an aged matched population without significant medical disorders.

Myostatin deficiency results in muscle hypertrophy and shifts muscle from aerobic toward anaerobic energy metabolism, resulting in reduced mitochondrial respiration, reduced expression of peroxisome proliferator-activated receptor (PPAR) transcriptional regulators, increased endonuclease activity and exercise induced lactic acidosis. This results in diminished exercise capacity and increased fatigability. This effect is exclusively regulated through myostatin signalling via ActRII. The essential effectors of the myostatin pathway are therefore biomarkers of the anabolic homeostatic state of the muscular tissue and can be used for pre-symptomatic monitoring of muscle atrophy or muscle wasting conditions, and/or for monitoring the effects of therapy on such conditions.

The method for determining anabolic capacity of the skeletal muscle system of a subject may further comprise comparing one or more of the levels of myostatin, ActRII receptor and/or follistatin to thresholds to determine the activity of the muscle wasting process. Optionally the subject may be treated with a dystrophin or MTM1 gene or pathology correcting therapy and/or a myostatin pathway inhibitor.

The present invention also provides a method for determining inclusion of subjects into a clinical trial for evaluation of a myostatin pathway inhibitor, the method comprising: (a) determining a level of myostatin and/or ActRII and/or follistatin in at least one muscle biopsy obtained from a treatment target muscle in a subject having or suspected of having muscle atrophy or a muscle wasting condition; (b) determining a level of myostatin and/or follistatin in a systemic sample obtained from the patient, wherein if: (i) the level of myostatin in the systemic sample is higher than a threshold and/or if the level of follistatin in the sample is lower than a threshold; and (ii) the level of myostatin and/or ActRII receptor in the at least one biopsy sample is higher than a threshold level and/or if the level of follistatin in the at least one biopsy sample is lower than a threshold level, admitting the subject to the clinical trial.

Additionally or alternatively, the method may comprise determining levels of activin A in the muscle biopsy and systemic samples, wherein if the level of activin A is higher than threshold levels for each sample, the patient is admitted into the clinical trial. Myostatin and activin A are both biomarkers of muscle health and atrophy. Activin A levels are indicative of myostatin levels and can therefore provide an indication of whether a subject is likely to respond to an anti-myostatin approach. Similarly, myostatin levels are indicative of activin A levels and can therefore provide an indication of whether a subject is likely to respond to an anti-activin A approach.

The method for determining inclusion of subjects into a clinical trial for evaluation of a myostatin pathway inhibitor may further comprise commencing the clinical trial and administering the myostatin pathway inhibitor or a placebo control to the subject.

The present invention additionally provides a method for determining whether a patient having or suspected of having spinal muscular atrophy (SMA) will respond to treatment, the method comprising: determining a level of myostatin and/or follistatin and/or Growth differentiation factor 11 (GDF11) in a systemic sample obtained from the patient; wherein a level of GDF11 above a threshold is associated with SMA; and wherein if the level of myostatin is higher than a threshold and/or if the level of follistatin in the sample is lower than a threshold, the patient will respond to treatment.

Spinal muscular atrophy (SMA) is a rare neuromuscular disorder characterised by loss of motor neurons and progressive muscle wasting, often leading to early death. The disorder is caused by a genetic defect in the SMN1 gene, which encodes SMN, a protein widely expressed in all eukaryotic cells and necessary for survival of motor neurons. Lower levels of the protein results in loss of function of neuronal cells in the anterior horn of the spinal cord and subsequent system-wide atrophy of skeletal muscles.

Spinal muscular atrophy manifests in various degrees of severity, which all have in common progressive muscle wasting and mobility impairment. Proximal muscles and respiratory muscles are affected first. Other body systems may be affected as well, particularly in early-onset forms of the disorder. SMA is the most common genetic cause of infant death. Due to the severity of its effects (which may affect the respiratory muscles) and the age of patients (who are commonly in infancy), it is often not possible to obtain a muscle biopsy sample, especially if a general anaesthetic would be required. However, the present inventors have determined that there is an association between abnormally high levels of systemic GDF11 and SMA. This may be an indication that GDF11 can be used in combination with other systemic markers of the myostatin pathway to determine whether a patient will be suitable for therapy to treat SMA.

GDF11, also known as bone morphogenetic protein 11 (BMP-11), is a myostatin(GDF8)-homologous protein that acts as an inhibitor of nerve tissue growth. Like myostatin, GDF11 binds to the ActII receptor. GDF11 has been shown to suppress neurogenesis through a pathway similar to that of myostatin, including stopping the progenitor cell-cycle during G-phase. The similarities between GDF11 and myostatin imply that similar signalling pathways are used to control tissue growth during both muscular and neural development.

As described above, suitable systemic samples for use in methods of the present invention include bodily fluid samples, such as a whole blood sample, a serum sample, a plasma sample or a urine sample. Preferably the systemic sample is a serum sample.

The method may further comprise administering a treatment for SMA, such as Nusinersen, to a patient determined to respond to the treatment.

Additionally or alternatively, the method may comprise determining levels of GDF11 in a subject with spinal muscular atrophy and, if levels are above a threshold of above 50-100% of normal, treating such a subject with a GDF11 inhibitor.

As described above, the patient and/or subject is preferably a mammal, including a human, and may be of any age or a paediatric or a geriatric patient. The patient may be an infant. In embodiments of the invention the patient may have or be suspected of having SMA.

Any number of the features of the various aspects of the invention may be combined with any number of features of any other aspects and in any embodiment.

The invention will now be described in detail, by way of example only, with reference to the figures.

FIGS. 1A-1D: Circulating levels of GDF8, FSTN, ACTIVIN A and GDF11

Circulating levels of either GDF8 (A), FSTN (B), ACTIVIN A (C) and GDF11 (D) were measured in healthy control (Ctrl, N=9), Becker Muscular Dystrophy (BMD, N=6), Spinal Muscular Atrophy (SMA, N=4), Duchenne Muscular Dystrophy (DMD, N=4), Inclusion Body Myositis (IBM, N=54), Myastenia Gravis (MG, N=12) or Facioscapulohumeral Dystrophy (FSHD, N=13) patients. Horizontal lines are medians, the extremities of the boxes are delimitated by the first and third quartile, and the whiskers correspond to the 10th and 90th percentile. A multiparametric analysis of variance and a Newman-Keuls post hoc test were performed. Degree of freedom=6.

Figure 2:
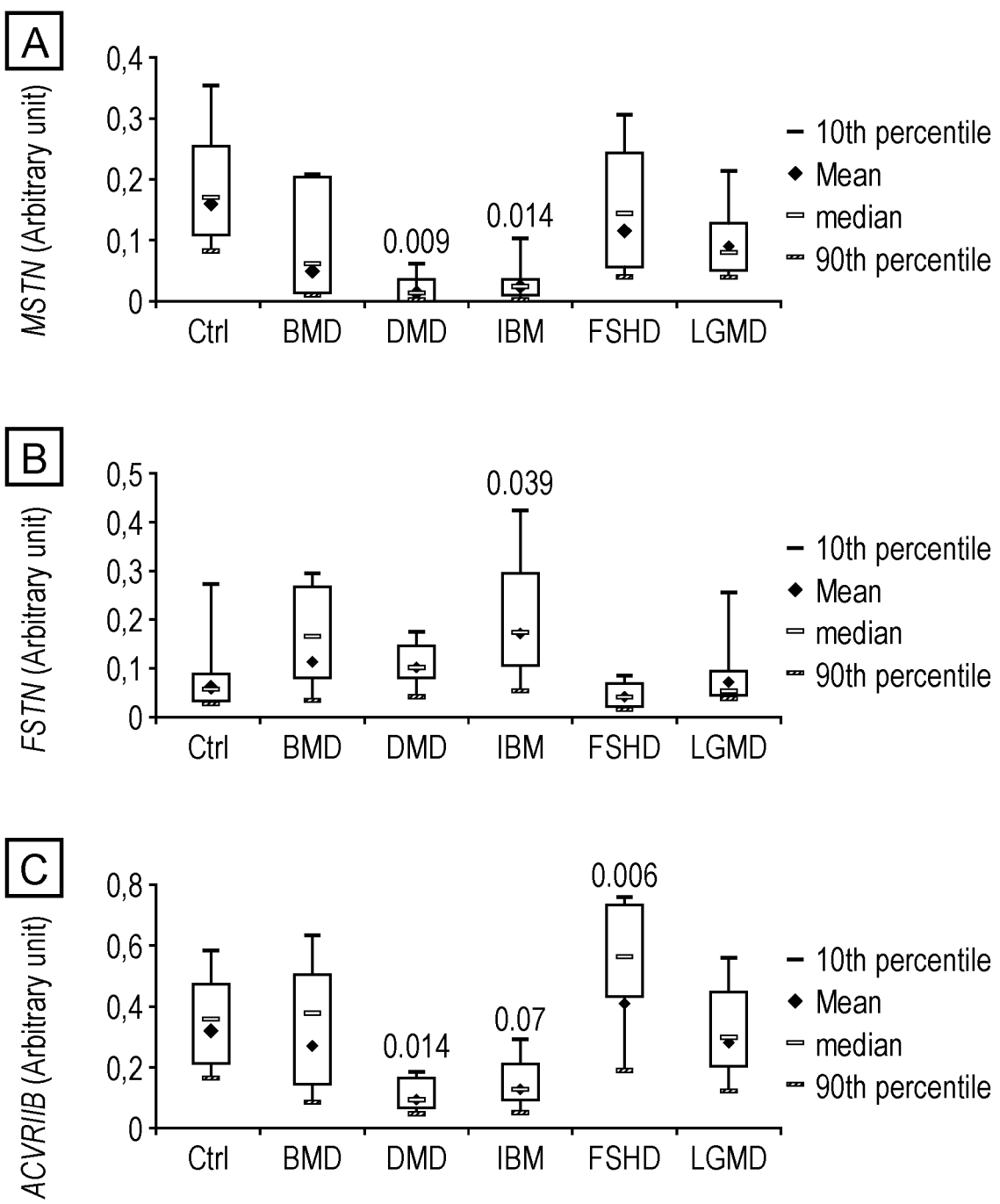

FIGS. 2A-2C: Myostatin pathway in muscle biopsies mRNA levels of either MSTN, FSTN, or ACTRIIB were measured by RT-qPCR in in healthy controls (Ctrl, N=9), Becker Muscular Dystrophy (BMD, N=6), Duchenne Muscular Dystrophy (DMD, N=17), Inclusion Body Myositis (IBM, N=17), Facioscapulohumeral Dystrophy (FSHD, N=13) or Limb Girdle Muscular Dystrophy (LGMD, N=11) patients. Horizontal lines are medians, the extremities of the boxes are delimitated by the first and third quartile, and the whiskers correspond to the 10th and 90th percentile. A multiparametric analysis of variance and a Newman-Keuls post hoc test were performed. Degree of freedom=6.

FIGS. 3A-3I: Myostatin network in Mtm1-KO mice.

The tibialis anterior (TAs) of 3 week-old Mtm1-KO mice were injected with either PBS (A, F, G, H, I), an AAV vector coding the myostatin pro-peptide D76A mutant (PropD76A) (A), an AAV vector coding Mtm1 (Mtm1) (F, G, H, I), or an AAV coding both Mtm1 and propD76A (F, G, H, I). Two weeks later, mice were sacrificed and the TAs were weighed (A, F). The weights (B), Msnt mRNA (C), Fsnt mRNA (D) or ActRIIb mRNA (E) were measured at 14, 21 or 30 days in the TAs of either Mtm1-KO mice (KO) or wild type littermates (WT).

FIG. 4A: Natural history of circulating myostatin levels in healthy and Golden Retriever muscular dystrophy (GRMD) dogs. While the myostatin level increases in healthy dogs as they age, it decreases in GRMD dogs. At the age of 2.5 months the myostatin level is sufficient to distinguish heathy and GRMD dogs. FIG. 4B: Locoregional injection of an AAV vector coding a dog microdystrophin. The injections restrict the myostatin decrease observed in GRMD dogs. FIGS. 4C and 4D: The systemic injection of a low or high dose of an AAV vector coding a dog microdystrophin is not sufficient to increase myostatin levels in GRMD dogs. Even after injection, myostatin level never reaches the levels observed in the WT animals. However, after high dose injection, myostatin level is maintained until the age of 20 months, while after low dose injection, myostatin level slowly decrease. Very interestingly, at the age of 25 months, myostatin levels suddenly fall and reach the levels observed in the non-injected animals. This probably highlights the moment when microdystrophin level is decreasing and the effect of AAV-microdystrophin therapy is waning. Indeed, after AAV injection, the muscle degeneration/regeneration cycle continues in the dogs because the treatment does not cure the animals. The microdystrophin transgene is therefore slowly cleared from the muscles leading to a decrease in microdystrophin and myostatin expression.

Figure 5:
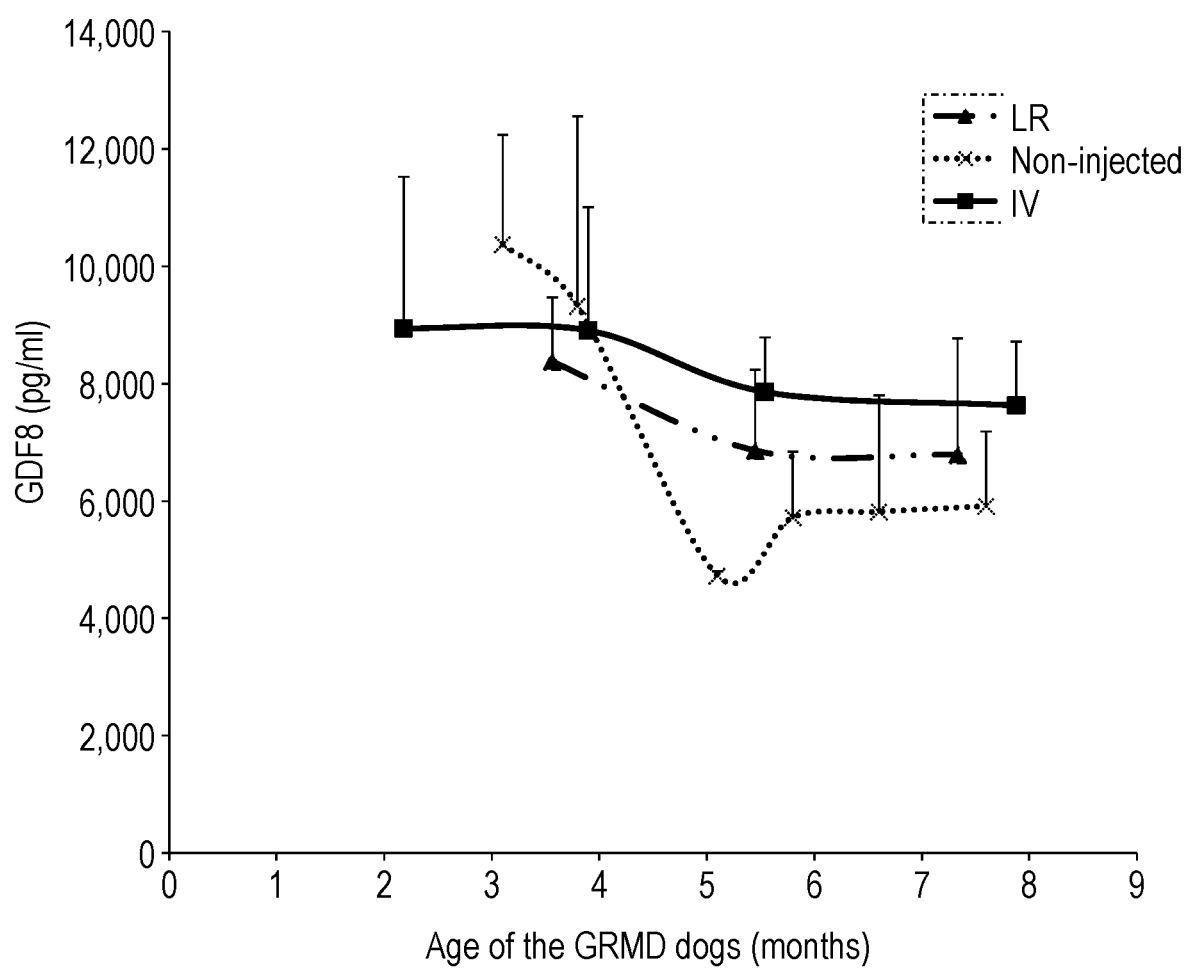

FIG. 5: The different elements of FIG. 4 are combined. A difference in circulating myostatin levels is observed in the low dose, high dose and untreated groups. The more microdystrophin is expressed, the higher the myostatin levels are.

EXAMPLES

Materials and Methods

Ethics Statement and Patient Reports

The collection of sera and biopsies were approved by the "Comite de Protection des Personnes" Paris VI and the French regulatory agency (ANSM) (CCP #99-12, ID RCB 2012-A01277-36), the research and Development Office (#DN 12DN29), and the East Central London Research Ethics Committee 1 (reference number 10/H0721/28). The characteristics of the patients are described in tables 1 and 2.

Mouse Experiments

Mice were handled according to French and European legislation on animal care and experimentation, and protocols were approved by the institutional ethical committee. The constitutive knockout of the myotubularin gene (Mtm1-KO, also named BS53d4-129pas) was described previously (Buj-Bello et al, 2002). Wild-type littermate males were used as controls.

Generation of Recombinant AAV Vector and Delivery

A recombinant serotype 1 AAV vector containing mutated myostatin propeptide D76A under the CMV promoter (AAV-PropD76A) was produced as previously described (Bartoli et al, 2007). Mouse Mtm1 cDNA (AF073996, NCBI) was cloned in the AAV expression pGG2-DES plasmid, which contains the human desmin promoter. Recombinant serotype 1 viral particles (AAV1-Mtm1) were obtained by a tri-transfection procedure from HEK293 cells as previously described (Buj-Bello et al, 2008). Vector titers were expressed as viral genomes per ml (vg/ml).

AAV vectors were intramuscularly delivered to 3 week-old KO mice and age matched wild type males. Mice were anesthetized by intraperitoneal injection of 5 µL/body gram of ketamine (20 mg/mL, Virbac) and xylazine (0.4%, Rompun, Bayer). Tibialis anterior (TA) muscles were injected with $3.5 \times 10^9$ vg of AAV-CMV-PropD76A, $5 \times 10^9$ vg of AAV-Mtm1 or sterile phosphate buffer saline (PBS) solution. Muscles were dissected 14 days after injection and frozen in either liquid nitrogen-cooled isopentane or liquid nitrogen for histological and molecular assays.

Measurement of MSTN, FSTN, GDF11 and ACTIVIN a in Blood Serum

Peripheral venous blood was collected from healthy and patients' volunteers using serum separator tubes (10 mL). After 30 minutes on the benchcoat at room temperature, the tubes were centrifuged at 2000 rpm for 10 min at 4° C. The collected serum (5 mL) was aliquoted and stored at −80° C. until further use. The concentrations of either GDF8, FOLLISTATIN, GDF11 or ACTIVIN A in the sera were mea-

TABLE 1

Characteristics of patients' sera

| | | Ctrl (n = 9) | BMD (n = 6) | SMA (n = 4) | DMD (n = 5) | IBM (n = 54) | MG (n = 12) | FSHD (n = 13) |
|---|---|---|---|---|---|---|---|---|
| Age (years) | Mean | 34.2 | 18.3 | 11.0 | 9.2 | 64.9 | 46.6 | 46.8 |
| | Range | 23.1-45.3 | 7.2-48.7 | 8.9-12.9 | 6.0-13.9 | 41.3-87.1 | 16.5-64.3 | 14.5-61.2 |
| Gender | Female | 6 | — | 1 | — | 17 | 7 | 4 |
| | Male | 3 | 6 | 3 | 5 | 37 | 5 | 9 |
| Age of onset | Mean | — | Early Childhood | Infant | Early Childhood | 56.5 | 37.3 | 20 |
| | Range | — | | | | 35-82 | 14.5-62.3 | 2-49 |

TABLE 2

Characteristics of patients' biopsies

| | | Ctrl (n = 9) | BMD (n = 6) | DMD (n = 17) | IBM (n = 17) | FSHD (n = 13) | LGMD (n = 11) |
|---|---|---|---|---|---|---|---|
| Age (years) | Mean | 43.2 | 32.5 | 9.7 | 70.5 | 45.0 | 28.8 |
| | Range | 24.0-69.0 | 1.6-61.3 | 0.8-17.7 | 56.9-81.0 | 13.0-79.4 | 8.6-57.9 |
| Gender | Female | 6 | — | — | 3 | 5 | 5 |
| | Male | 3 | 6 | 17 | 14 | 8 | 6 |
| Age of onset (years) | Mean | — | 23.8 | 3.3 | 65.4 | 27.2 | 23.3 |
| | Range | — | 5-48 | 2-6 | 45-78 | 16-40 | 2-55 | sured using an ELISA kit (respectively #DGDF8, #DFN00, #DY1958 and #DAC00B R&D Systems Europe, Ltd, Abingdon, United Kingdom) according to the manufacturer's instructions. The optical density was measured using a microplate reader (Infinite 200 Pro, Tecan Group Ltd., Mannedorf, Switzerland). Importantly, the myostatin immunoassay was designed to recognize mature GDF8. According to the manufacturer, no significant cross-reactivity or interference was observed in the presence of 50 ng/ml (20 times more than the highest value measured in our experiment) of different proteins including the GDF8 propeptide, GDF11 or GDF15. We have experimentally confirmed this result by using 4000 pg/ml of recombinant GDF11. The absence of cross reactivity with FOLLISTATIN (8000 pg/ml), ACTIVIN 1 (4000 pg/ml) and GASP-1 (4000 pg/ml) was also experimentally validated.

RNA Extraction, PCR and Real-Time PCR

For murine samples, Total RNA was purified from muscles of 5 week-old males using TRIzol reagent (Life Technologies, Saint Aubin, France) according to manufacturer's instructions. RNA concentration was measured by spectrophotometry (OD 260 nm) using a nanodrop ND-1000 spectrophotometer (Thermo Scientific, Wilmington, Del., USA) and RNA integrity was verified by electrophoresis using ethidium bromide. After DNAse treatment (Ambion), RNA was reverse transcribed using Super Script II RNase H Reverse Transcriptase (Invitrogen) in the presence of Random Primers (Promega). Real-time PCR was performed at 60° C. as melting temperature and with primers described in Table 3 using an ABI Prism 7900 apparatus (Applied Biosystems) in a final volume of 25 µl with reverse transcriptase, forward and reverse primers (0.5 nmol/ml) and SYBRGreen Mastermix (Roche, Basel, Switzerland).

TABLE 3

Oligonucleotides used in this study

| Gene symbol | Accession no | Name | 5' 3' | SEQ ID NO | Amplicon length |
|---|---|---|---|---|---|
| Actb | NM_007393.5 | b-actin_F | CTGGCTCCTAGCACCATGAA | 1 | 123 |
|  |  | b-actin_R | CTGCTTGCTGATCCACATCT | 2 |  |
| Activin A | NM_008380.2 | Activin A-F | CACACTTCTGCACGCTCCAC | 33 | 92 |
|  |  | Activin A-R | TTTGCCGAGTCAGGCACAG | 34 |  |
| Tubb5 | NM_011655.5 | b-tubulin_F | CCTTCATTGGAAACAGCACA | 3 | 222 |
|  |  | b-tubulin_R | CCTCCTCTCCGAAATCCTCT | 4 |  |
| Gapdh | NM_001289726.1 | Gapdh_F | TTGTGATGGGTGTGAACCAC | 5 | 283 |
|  |  | Gapdh_R | TTCAGCTCTGGGATGACCTT | 6 |  |
| Gdf11 | NM_010272 | Gdf11-F | ATCAGCCGGGAGGTAGTGAA | 35 | 159 |
|  |  | Gdf11-R | CTGGGCCATGCTTATGACCGT | 36 |  |
| Hprt | NM_013556.2 | Hprt1_F | GCAAACTTTGCTTTCCCTGG | 7 | 85 |
|  |  | Hprt1_R | ACTTCGAGAGGTCCTTTTCACC | 8 |  |
| Rplp0 | NM_007475.5 | P0_F | CTCCAAGCAGATGCAGCAGA | 9 | 87 |
|  |  | P0_R | ATAGCCTTGCGCATCATGG | 10 |  |
| Acvr2b | NM_007397.3 | ActrIIB_F | GCTCAGCTCATGAACGACT | 11 | 68 |
|  |  | ActrIIB_R | CTCTGCCACGACTGCTTGT | 12 |  |
| Fst | NM_001301373.1 | Fstn_F | CTCTTCAAGTGGATGATTTTC | 13 | 345 |
|  |  | Fstn_R | ACAGTAGGCATTATTGGTCTG | 14 |  |
| Mstn | NM_010834.3 | Mstn_F | GCACTGGTATTTGGCAGAGTA | 15 | 345 |
|  |  | Mstn_R | CACACTCTCCTGAGCAGTAAT | 16 |  |
| INHIBIN A | ENST00000242208.4 | F-ACTIVIN A | TTATGGAGCAGACCTCGGAG | 37 | 75 |
|  |  | R-ACTIVIN A | AAATCTCGAAGTGCAGCGTC | 38 |  |
| B2M | NM_004048 | F_B2M | CTCTCTTTCTGGCCTGGAGG | 17 | 67 |
|  |  | R_B2M | TGCTGGATGACGTGAGTAAACC | 18 |  |
| GAPDH | ENST00000229239 | F-GAPDH2 | AAGGTGAAGGTCGGAGTCAACGG | 19 | 199 |
|  |  | R-GAPDH2 | TGACAAGCTTCCCGTTCTCAGCC | 20 |  |
| GUS | ENST00000304895 | F-GUS | CTCATTTGGAATTTTGCCGATT | 21 | 81 |
|  |  | R-GUS | CCGAGTGAAGATCCCCTTTTTA | 22 |  |
| RPLP0 | ENSG00000089157 | F-P0 | TCCAGGCTTTAGGTATCACCAC | 23 | 94 |
|  |  | R-P0 | GCTCCCACTTTGTCTCCAGTC | 24 |  |
| PPIA | ENST00000355968 | F-PPIA | CCTAAAGCATACGGGTCCTG | 25 | 133 |
|  |  | R-PPIA | TTTCACTTTGCCAAACACCA | 26 |  |
| ACVR2B | ENST00000352511 | F52-AcvRIIb | CCTCTCTGGGGATCGCTGT | 27 | 84 |
|  |  | R135-AcvRIIb | CTCCCAGTTGGCGTTGTAGT | 28 |  |

TABLE 3-continued

Oligonucleotides used in this study

| Gene symbol | Accession no | Name | 5' 3' | SEQ ID NO | Amplicon length |
|---|---|---|---|---|---|
| FST | ENST00000256759 | F1-FST | CGGCTGAGCACCTCGTG | 29 | 155 |
| | | R1-FST | TTCTTGTTCATTCGGCATTT | 30 | |
| GDF11 | ENST00000257868.9 | F-GDF11 | ATTGGCAGAGCATCGACTTC | 39 | 182 |
| | | R-GDF11 | TTTTGTGTTCTCTAGGACTCG | 40 | |
| MSTN | NM_005259 | F-972 | TTTTACCCAAAGCTCCTCCA | 31 | 258 |
| | | R-3017 | GAGTCTCGACGGGTCTCAAA | 32 | |
| MYL1 | ENST00000352451 | F-MYL1 | GCAATGAAGAGCTGAATGCCA | 41 | 126 |
| | | R-MYL1 | TGTCAAAGACACGCAGACCCT | 42 | |

For human samples, cryopreserved tissues were transferred in tube containing 1.4 mm ceramic beads (Precellys, Bertin Corp, Maryland, United State) plus 1 mL of Trizol (Life technologies, Saint Aubin, France) and shaken 3 times at 5700 rpm for 30s. Between each cycle, tubes were incubated in ice during at least 1 min. Total RNAs were extracted using trizol according to the manufacturer's protocol (Life technologies, Saint Aubin, France). The quantity of RNA was determined using a nanodrop ND-1000 spectrophotometer (Thermo Scientific, Wilmington, Del., USA). The reverse transcription and polymerase chain reaction (PCR) were described previously 29. qPCRs were performed on a LightCycler 480 Real-Time PCR System (Roche, Meylan, France) in a final volume of 4 µl with 0.4 µl of reverse transcriptase (RT) product, 0.18 µl each of forward and reverse primers (20 pmol/ml) and 4.5 µl of SYBRGreen Mastermix (Roche, Basel, Switzerland). After qPCR, the PCR products were run on a 2% agarose gel and were cloned using the Topocloning kit (Life Technologies, Saint Aubin, France) and sequenced. Primers used in this study are described in Table 3.

Quantitative PCR (qPCR) was designed according to the MIQE standards 30. Among the 87 items to review, 57 were classified as essential. All were followed. In particular, to determine the best human housekeeping gene, 5 genes were evaluated: B2M, GAPDH, GUS, PO and PPIA. A MANOVA test has demonstrated that none of these genes were suitable for housekeeping since significant statistical changes were observed between the different groups. GUS, PO and PPIA were then chosen to calculate the expression normalization factor for each sample using geNorm software (V3.5). To determine the best housekeeping mouse gene, 6 genes were evaluated: Gapdh, Po, Hprt1, β-actin, β-tubulin and 18S and Po was chosen.

Statistical Analysis

A one-way ANOVA was used for all the experiments, followed by the Fisher's Least Significant Difference multiple comparison test. Differences were considered to be statistically different at p*<0.05; <0.01; *<0.001

Results

Human Myostatin Serum Concentrations are Lowest in the Most Marked Muscle Atrophying Diseases Serum concentrations of MSTN, FSTN, GDF11 and ACTIVIN A were determined in patients with different pathologies affecting skeletal muscles (summarized in Table 1). BMD (Becker Muscular Dystrophy) and DMD (Duchenne Muscular Dystrophy) share similar clinical signs and symptoms including muscle weakness and atrophy but in BMD, symptoms are milder and patients have a later onset. Both DMD and BMD are caused by different mutations in the DMD gene but mutations in DMD patients lead to an absence of any functional dystrophin protein whereas mutations in BMD patients lead to a less functional protein. SMA (Spinal Muscular Atrophy) is characterized by a loss of motor neurons leading to muscle wasting often leading to premature death. IBM (Inclusion-Body Myositis) is the most common age-related muscle disease in elderly and is a slowly progressive inflammatory and degenerative myopathy characterized by chronic muscle weakness and atrophy. FSHD (Facioscapulohumeral Dystrophy) is the most common muscular dystrophy in adults characterized by the selective atrophy of groups of muscles. Finally, MG (Myasthenia Gravis) is the most common primary disorder of neuromuscular transmission, caused by antibodies to the acetylcholine receptor leading to muscle weakness usually without severe muscle atrophy. For ACTIVIN A, no differences were observed but a trend to a lower expression in SMA and DMD patients (p=0.06 for both) was noted. No modification of GDF11 was noted, except in SMA sera in which a massive overexpression was observed. Concerning GDF8, in the most atrophic (SMA) and most wasting (DMD) muscle diseases studied a two-fold or higher decrease of circulating MSTN was observed (SMA 30.6%±13.7 and DMD 50.6%±17.18 MSTN compared to controls respectively) (FIG. 1A). Associated with this MSTN decrease, an important trend to an increase of circulating FSTN was observed (SMA 135.6%±71.3 and DMD 189.4%±35.2 compared to controls respectively) (FIG. 1B).

BMD, IBM and FSHD patients, who clinically show a less pronounced muscle atrophy, have more circulating myostatin than DMD and SMA patients but less than controls (BMD 71%±23.7, IBM 71%±55.6 and FSHD 66%±35 compared to controls respectively). The levels of circulating FSTN were not increased in BMD patients (85.5%±22.4) whereas a trend to an increase was observed in both IBM and FSHD patients (146.3±70.9 and 145.8±72.8). In MG patients, who do not show any atrophy, no modification of MSTN nor FSTN was observed. Importantly, regarding all the effectors of the myostatin pathway, an important variation across samples is observed in IBM and FSHD patients, suggesting that the myostatin network may be significantly down-regulated in some patients whereas there is still preserved myostatin expression in others. A correlation test was performed between MSTN and FSTN levels, but no correlation was found.

The MSTN pathway is down-regulated at mRNA level in the most atrophying diseases As MSTN is mainly produced by skeletal muscle, the mRNA expression levels of several genes implicated in the myostatin pathway were investigated in muscle biopsies (summarized in Table 2). Unfortunately, SMA biopsy could not be studied since the diagnosis is essentially genetic and a muscle biopsy is not normally performed in SMA. A massive down-regulation of MSTN was observed in both the DMD and IBM patients as only 29% and 12% of the respective mRNA levels were detectable (FIG. 2A). At the same time, FSTN was up-regulated by 2.7 fold in IBM patients (p=0.039) (FIG. 2B). Interestingly, the myostatin receptor ActRIIB was strongly down-regulated in both DMD (30% of residual mRNA, p=0.014) and IBM (40% of residual mRNA, P=0.07) but up-regulated in FSHD (+28%, p=0.006) (FIG. 2C). In LGMD and BMD, no significant modification of muscle MSTN, FSTN or ACTRIIB was observed. An important variability across LGMD and BMD samples was observed but the most atrophying diseases (DMD, SMA) showed again a general down-regulation of the myostatin pathway. No correlation was found between MSTN, ACTRIIB and FSTN in all individual diseases. However, concerning FSHD patients, FSHD1 patients express less MSTN than FSHD2 patients (p=0.048), but no difference was observed in FSTN (data not shown). FSHD2 patients showed a trend to express more ACTRIIB than FSHD1 (+120%, p=0.08).

Expression of Myostatin is Crucial for a Successful Anti-Myostatin Approach

In order to determine whether or not the endogenous expression level of the myostatin pathway could impact the success of anti-myostatin approaches, we used the Mtm1-KO mouse model. We have chosen the Mmt1-KO model because X-linked myotubular myopathy (XLMTM), which is a severe congenital disease due to mutations in the myotubularin coding gene MTM1, is characterized by generalized muscle hypotrophy and weakness and this mouse model recapitulates the muscle atrophy. Moreover, the XLMTM muscle phenotype can be corrected by AAV-mediated gene replacement therapy in the Mtm1-KO mouse model of the disease.

Figure 3:
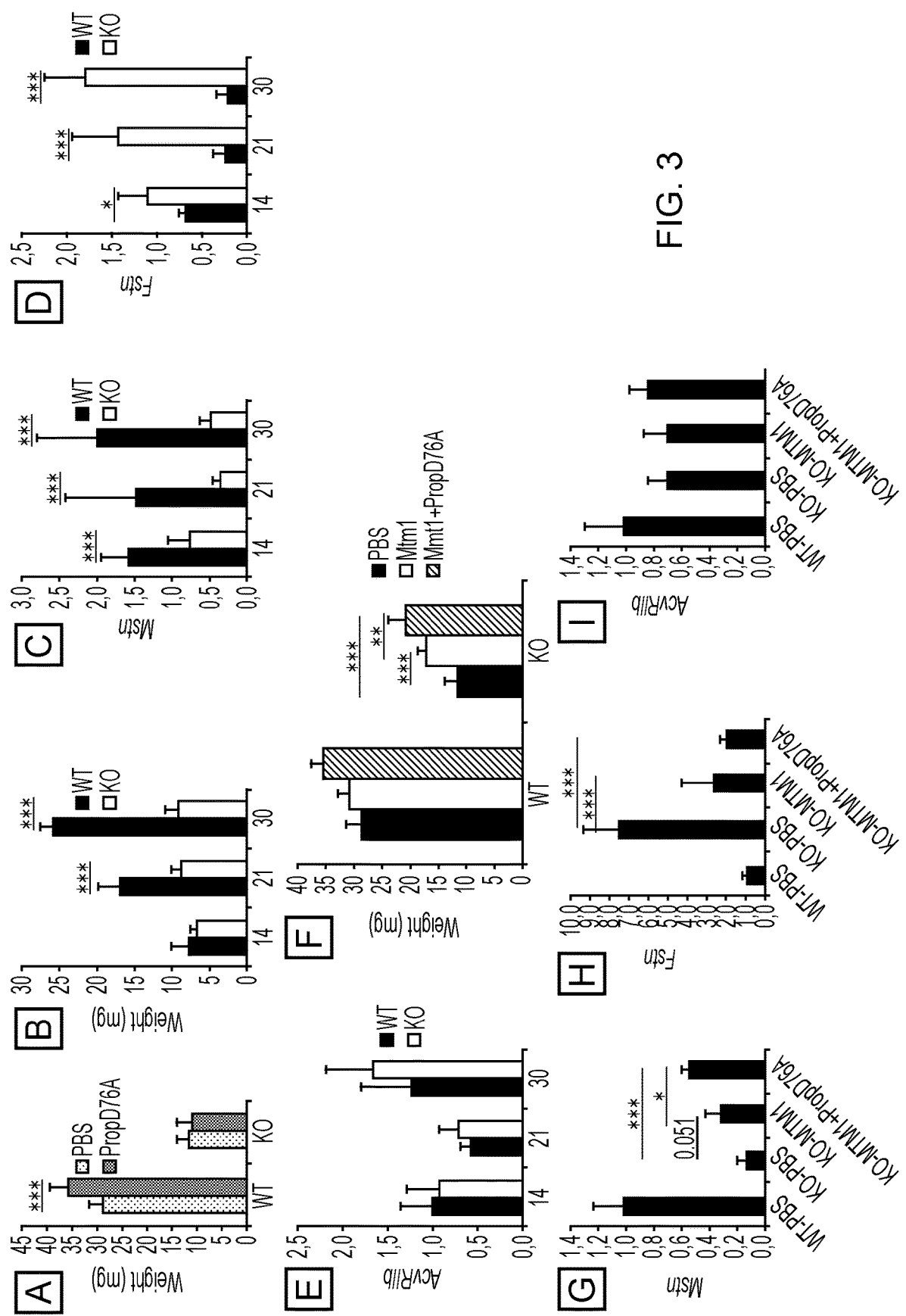

Three week-old myotubularin KO (Mtm1-KO) and wild type (WT) mice were intramuscularly (in the tibialis anterior (TA)) injected with an AAV coding the myostatin pro-peptide D76A mutant (AAV8PropD76A). While an increase in muscle weight was observed in the WT mice after 1 injection (123.8%±12.7% of residual mRNA, p=1.16.10e-10), no muscle growth was observed in the Mtm1-KO mice (93.7%±26.9 of residual mRNA, p>0.05) (FIG. 3A). Because at 3 weeks, Mtm1-KO mice already show an important loss of muscle weight compared to WT littermates (84%±12% of residual mRNA at 14 days, 50%±8.1% at 21 days and 34,5%±7.2% at 30 days in tibialis anterior, FIG. 3B), the expression level of the myostatin network was investigated. A strong down expression of Mstn (47.6%±18.6% of residual mRNA at 14 days, 22.5%±7.8% at 21 days and 25%±6.5% at 30 days, FIG. 3C), associated with a massive up-regulation of Fstn (159%±44.9% of residual mRNA at 14 days, 567%±201% at day 21 and 768%±190% at day 30, FIG. 3D) was observed. ActRIIb expression was only barely affected (FIG. 3E). These results suggest that inhibiting the myostatin pathway might not be a successful therapeutic strategy in the Mtm1-KO mice at the time point of our analysis because the myostatin pathway is already dramatically down-regulated with 4.4 fold decrease of Mstn mRNA and a 5.6 fold increase of Fstn mRNA in the TA of 3 weeks old Mtm1-KO mice.

The tibialis anterior of WT or Mtm1-KO mice were next intramuscularly injected with either an AAV coding the Mtm1 gene (AAV-Mtm1) or a combination of the AAV-Mtm1 gene and the AAV16 PropD76A. In the presence of the Mtm1 protein, muscle histology was greatly improved with an increase of cross-sectional fiber size, and an improved intracellular architecture revealed after NADH-TR staining (data not shown). The abnormal localizations of the dihydropyrine 1α receptor (DHPR1α) and ryanodine receptor 1 (RYR1) were partially restored. In the Mtm1-KO mice, the muscle mass was improved in the presence of the AAV-Mtm1 (148.1%±12.9% of residual mRNA, p=5.3 10e-6 compared to the Mtm1 KO injected with PBS) whereas no modification of muscle mass was observed in the WT mice (FIG. 3F). Interestingly, the presence of both AAV-Mtm1 and AAV-PropD76A allowed a further increase in muscle mass in the Mtm1-KO mice (179%±25.2%, p=7.15 10e-11, compared to the TAs injected with PBS, FIG. 3F). A similar effect was observed in the WT mice (123.3%±6.8%, p=8.5 10e-9 compared to the WT mice injected with PBS). Importantly, in both Mtm1-KO and WT mice, the simultaneous injection of AAV-PropD76A+AAV-Mtm1 led to a higher increase in muscle mass than AAV-Mtm1 alone (FIG. 3F).

To determine if the myostatin pathway was restored by the expression of Mtm1 in the Mtm1-KO mice, the expression levels of Mstn, Fstn and ActRIIb were analyzed in the transduced TAs. An increase of Mstn, associated with a decrease of Fstn was observed in the presence of Mtm1 (FIG. 3G, H), without modification of ActRIIb level (FIG. 3I). The combination of myostatin pathway inhibition and Mtm1 rescue enhanced both the Mstn increase and the Fstn decrease (FIG. 3G, H). These results suggest that the expression of Mtm1 in the Mtm1-KO mice leading to a 2.4 increase of Mstn and a 2.8 decrease of Fstn was sufficient to enable an anabolic effect of the myostatin propeptide on muscle mass. The muscle atrophy observed in the Mtm1-KO mice may not be due to an up-regulation of the myostatin pathway but rather a consequence of the absence of myotubularin.

DISCUSSION

During the past 12 years at least 15 clinical trials aimed at inhibiting the myostatin pathway have been carried out to improve muscle mass and function in muscular diseases, and several of these studies are still underway (https://clinicaltrials.gov/). Different pathologies were targeted among them BMD, DMD, LGMD, IBM and FSHD. The concept of anti-myostatin therapy for neuromuscular diseases has been based on the postulate that inhibiting this pathway in patients might lead to an increase in muscle mass and muscle strength/function as it does in normal muscle, which implies that the level of circulating myostatin is high enough to be down-regulated by such a therapeutic approach. However, the results were disappointing: (i) the injection of MYO-29, a recombinant human neutralizing antibody to myostatin, in adult muscular dystrophies (BMD, FSHD and LGMD) did not improve any of the outcome measures (strength, lean body mass, muscle volume). (ii) DMD patients treated with ACE-031, a soluble form of activin type IIB receptor, showed a very slight increase in total body lean mass (+4.1% compared to +2.6% in the placebo group) and a non-statistically significant trend for maintenance of 6 minute walk test was observed in the ACE-031 treated group, although the study had to be interrupted after 12-16 weeks due to safety concerns. (iii) For sIBM patients treated with bimagrumab, a human monoclonal antibody targeting activin receptors IIA and IIB, an increased muscle and lean body mass was observed, as well as an improvement in the 6-minute walking test after 6 month treatment in a single dose phase 2 study. However, Novartis has recently announced that bimagrumab had not met its primary endpoint (6-minute walk distance) in a late-stage Phase2b/3 study. (iv) Only one approach in phase 2 showed preliminary promising results: BMD patients, multiply intramuscularly injected in 3 of the 4 muscles forming the quadriceps with an AAV vector encoding the follistatin isoform FS344 showed an improvement of the 6 minute walk test by 11.5% at 6 months post injection. Currently, several clinical trials are underway and results are expected next year.

Different possibilities could explain this absence of functional improvement, among them the drug pharmacokinetic/pharmacodynamic (PK/PD) in the conditions studied so far in humans. A retrospective analysis demonstrated that central clearance of MYO-029 in humans is greater than 2 fold than typical IgG1 mAbs and PK/PD analyses in monkeys suggesting that peak and steady state exposures in the MYO-029 trial might achieve only 50% and 10% of the maximum effect seen in monkeys. This would explain why the MYO-029 had a low probability to induce a muscle mass increase in patients. Another explanation could be the lack of specificity of the drugs themselves, MSTN and GDF11 sharing 90% in their mature region for example. Finally, MSTN might not be the only ligand implicated in muscle growth to bind ACTRIIB, as it was demonstrated that blocking ActRIIb in Mstn deficient mice further enhances muscle mass.

In our study, we have explored another confounding possibility based on the expression levels of circulating and muscle-endogenous proteins implicated in the myostatin pathway. Recently, Burch et al. (2017) have published that serum myostatin concentrations are reduced in patients with muscle diseases. They concluded that because myostatin is mainly produced by muscle tissue, these reduced circulating myostatin may reflect the net loss of functional muscle mass. Our data however do not support this hypothesis. Indeed, we have observed that whole myostatin pathway is strongly altered in the most atrophying neuromuscular diseases, at both mRNA and protein levels, and that the lower expression of serum myostatin is associated with a reduced muscle expression of MSTN mRNA. These results indicated that reduced circulating myostatin levels are not, or at least not only, the reflexion of muscle loss but represent an altered myostatin homeostasis of the diseased tissue. In addition, the muscle atrophy observed in DMD patients is not the consequence of an activation of the myostatin pathway. On the contrary, our data indicate that the myostatin pathway may be intrinsically down-regulated in atrophying or wasting muscle diseases to counterbalance the wasting process. This could explain the apparent contradictory results in mice and humans regarding the efficacies of anti-myostatin approaches. Indeed, the outcome of a clinical trial in DMD patients was not encouraging, while myostatin pathway blockade has been successful in mdx mice. Despite the fact that Duchenne patients and mdx mice share a mutation in the same gene, no important muscle atrophy is observed before 6 months of age in the mdx mouse and experiments are usually performed before this age. Moreover, even if myostatin levels are lower in mdx mouse than in wild type mouse, the endogenous circulating myostatin level is at least 50 times higher in mice than in humans. This could be one of the reasons why anti-myostatin approaches in the mdx model were successful.

Finally, one of the most important questions raised by our work concerns the usefulness of blocking the myostatin pathway in neuromuscular diseases in general. In slowly progressive pathologies such as BMD or FSHD, an important variability of both myostatin and follistatin circulating proteins is observed across samples, suggesting that at least some patients may be eligible for an anti-myostatin approach. However, in the most wasting neuromuscular diseases such as DMD, the whole myostatin pathway is down-regulated. Interestingly, in the Mtm1-KO mouse model, the restoration of Mtm1 expression is associated with a normalisation of the Mstn pathway, indicating by analogy that at least partial restoration of the dystrophin protein might be necessary before the inhibition of myostatin. Such an assumption is supported by the higher circulating myostatin levels in BMD compared to DMD, and experimentally by the stronger effect of anti-myostatin therapy in mdx mice if complemented by dystrophin restoration through exon skipping. Therefore, for future trials of anti-myostatin therapy patient eligibility should be tested by ascertaining sufficient levels of the therapy target and taking into account that general circulating myostatin levels may not be representative of the muscle-intrinsic levels of affected target muscles. Furthermore, in the most atrophying diseases, the mutated gene might need to be rescued first in order to restore myostatin expression before inhibiting the myostatin pathway becomes a therapeutic option.

Example 2

Golden Retriever muscular dystrophy (GRMD) dog samples were obtained from either the Boisbonne center for gene therapy or the Ecole Nationale Veterinaire d'Alfort. Some dogs have been locoregionaly (single administration of $1\times10^{13}$ vg/kg via transvenous perfusion of one forelimb) or systemically (single dose of $1\times10^{14}$ vg/kg or $1\times10^{13}$ vg/kg) treated with a rAAV2/8 vector encoding a canine microdystrophin, as described in Le Guiner et al (Nat Comms, 2017).

Injected dogs were monitored for several months and blood samples were collected at different time before the dogs were euthanized.

The concentrations of GDF8 were assessed by ELISA (#DGDF80, R&D Systems Europe, Ltd, Abingdon, United Kingdom) according to the manufacturer's instructions. The optical density was measured using a microplate reader (Infinite 200 Pro, Tecan Group Ltd., Mannedorf, Switzerland).

Results can be seen in FIGS. 4 and 5 and demonstrate that muscle wastage can be stabilised by gene therapy with a rAAV2/8 vector encoding a canine microdystrophin, particularly when the therapy is administered systemically at the high dose (FIG. 4D).

REFERENCES

M. Bartoli, J. Poupiot, A. Vulin, F. Fougerousse, L. Arandel, N. Daniele, C. Roudaut, F. Noulet, L. Garcia, O. Danos, and I. Richard, AAV-mediated delivery of a mutated myostatin propeptide ameliorates calpain 3 but not alpha-sarcoglycan deficiency, Gene therapy (2007).14 (9), 733.

A. Buj-Bello, V. Laugel, N. Messaddeq, H. Zahreddine, J. Laporte, J. F. Pellissier, and J. L. Mandel, The lipid phosphatase myotubularin is essential for skeletal muscle maintenance but not for myogenesis in mice, Proceedings of the National Academy of Sciences of the United States of America (2002). 99 (23), 15060.

A. Buj-Bello, F. Fougerousse, Y. Schwab, N. Messaddeq, D. Spehner, C. R. Pierson, M. Durand, C. Kretz, O. Danos, A. M. Douar, A. H. Beggs, P. Schultz, M. Montus, P. Denefle, and J. L. Mandel, AAV-mediated intramuscular delivery of myotubularin corrects the myotubular myopathy phenotype in targeted murine muscle and suggests a function in plasma membrane homeostasis, Human molecular genetics (2008). 17 (14), 2132.

S. Cohen, J. A. Nathan, and A. L. Goldberg, Muscle wasting in disease: molecular mechanisms and promising therapies, Nature reviews (2015). 14 (1), 58.

P. M. Burch, O. Pogoryelova, J. Palandra, R. Goldstein, D. Bennett, L. Fitz, M. Guglieri, C. M. Bettolo, V. Straub, T. Evangelista, H. Neubert, H. Lochmuller, and C. Morris, Reduced serum myostatin concentrations associated with genetic muscle disease progression, Journal of neurology (2017). 264(3):541-553.

L. W. Gamer, K. A. Cox, C. Small, V. Rosen, Gdf11 is a negative regulator of chondrogenesis and myogenesis in the developing chick limb. Developmental Biology (2001). 229(2):407-20.

C. Le Guiner, L. Servais, M. Montus, T. Larcher, B. Fraysse, S. Moullec, M. Allais, V. Francois, M. Dutilleul, A. Malerba, T. Koo, J-L Thibaut, B. Matot, M. Devaux, J. Le Duff, J-Y Deschamps, I. Barthelemy, S. Blot, I. Testault, K. Wahbi, S. Ederhy, S. Martin, P. Veron, C. Georger, T. Athanasopoulos, C. Masurier, F. Mingozzi, P. Carlier, B, Gjata, J-Y. Hogrel, O. Adjali, F. Mavilio, T. Voit, P. Moullier & G. Dickson, Long-term microdystrophin gene therapy is effective in a canine model of Duchenne muscular dystrophy, Nature Communications (2017). 8:16105.

Q. Jin, C. Qiao, J. Li, J. Li, X. Xiao, Neonatal Systemic AAV-Mediated Gene Delivery of GDF11 Inhibits Skeletal Muscle Growth, Molecular Therapy (2018). February 2. pii: S1525-0016(18)30023-6.

J. E. Jones, S. M. Cadena, C. Gong, X. Wang, Z. Chen, S. X. Wang, C. Vickers, H. Chen, E. Lach-Trifilieff, J. R. Hadcock, D. J. Glass, Supraphysiologic Administration of GDF11 Induces Cachexia in Part by Upregulating GDF15, Cell Reports (2018). 22(6):1522-1530.

Latres E, Mastaitis J, Fury W, Miloscio L, Trejos J, Pangilinan J, Okamoto H, Cavino K, Na E, Papatheodorou A, Willer T, Bai Y, Hae Kim J, Rafique A, Jaspers S, Stitt T, Murphy A J, Yancopoulos G D, Gromada J, Activin A more prominently regulates muscle mass in primates than does GDF8, Nature Communications (2017). 8:15153

---

The invention claimed is:

1. A method for determining whether a subject having or suspected of having a muscle atrophy or a muscle wasting condition will respond to treatment with a myostatin pathway inhibitor, the method comprising:
   (a) measuring a level of myostatin in a systemic sample obtained from the subject,
   (b) selecting a subject wherein the level of myostatin in the systemic sample is higher than myostatin levels in systemic samples from individuals with significant muscle atrophy and/or severe or advanced muscle wasting conditions, but below myostatin levels in systemic samples from healthy individuals; and (c) administering a myostatin pathway inhibitor to the subject of (b).

2. The method according to claim 1, wherein the myostatin is measured as protein or mRNA.

3. The method according to claim 1, wherein the myostatin is measured in a pro-peptide or mature protein form.

4. The method according to claim 1, wherein the systemic sample is a whole blood sample, a serum sample, a plasma sample or a urine sample.

5. The method according to claim 1, wherein the muscle atrophy or muscle wasting condition is a muscle dystrophy; a central or spinal muscular atrophy; a neurogenic muscular atrophy; a congenital myopathy; or an 'idiopathic' muscle wasting condition.

6. The method according to claim 1, wherein the myostatin pathway inhibitor is a myostatin antagonist or an ActRII antagonist.

7. The method according to claim 6, wherein the myostatin antagonist is an anti-myostatin antibody, a myostatin decoy, a follistatin or a follistatin analogue.

8. The method according to claim 6, wherein the ActRII antagonist is an anti-ActRII antibody, an ActRII decoy or an inhibitor of effectors downstream of the ActRII.

9. A method for treating muscle atrophy or a muscle wasting condition, the method comprising:
   (a) measuring a level of myostatin in a systemic sample obtained from a subject having or suspected of having the muscle atrophy or the muscle wasting condition;
   (b) selecting a subject wherein the level of myostatin in the systemic sample is higher than myostatin levels in systemic samples from individuals with significatn muscle atrophy and/or severe or advanced muscle wasting conditions, but below myostation levels in systemic samples from healthy individuals;and
   (c) administering a treatment for the muscle atrophy or the muscle wasting condition to the subject of (b).

10. A method for determining inclusion of a subject, having or suspected of having muscle atrophy or a muscle wasting condition into a clinical trial for evaluation of a myostatin pathway inhibitor, the method comprising:
    (a) measuring a level of myostatin in a systemic sample obtained from the subject,
    (b) selecting a subject wherein the level of myostatin in the systemic sample is higher than myostatin levels in systemic samples from individuals with significant muscle atrophy and/or severe or advanced muscle wasting conditions, but below myostatin levelss in systemic samples from healthy individuals; and
    (c) including the subject of (b) in the clinical trial;
    (d) commencing the clinical trial; and
    (e) administering the myostatin pathway inhibitor to the subject.

11. The method according to claim 9, wherein the myostatin is measured as protein or mRNA.

12. The method according to claim 9, wherein the myostatin is measured in a pro-peptide or mature protein form.

13. The method according to claim 9, wherein the systemic sample is a whole blood sample, a serum sample, a plasma sample or a urine sample.

14. The method according to claim 9, wherein the muscle atrophy or muscle wasting condition is a muscle dystrophy; a central or spinal muscular atrophy;
    a neurogenic muscular atrophy; a congenital myopathy; or an 'idiopathic' muscle wasting condition.

15. The method according to claim 9, wherein the myostatin pathway inhibitor is a myostatin antagonist or an ActRII antagonist.

16. The method according to claim 15, wherein the myostatin antagonist is an anti-myostatin antibody, a myostatin decoy, a follistatin or a follistatin analogue.

17. The method according to claim 15, wherein the ActRII antagonist is an anti-ActRII antibody, an ActRII decoy or an inhibitor of effectors downstream of the ActRII.

18. The method according to claim 10, wherein the myostatin is measured as protein or mRNA.

19. The method according to claim 10, wherein the myostatin is measured in a pro-peptide or mature protein form.

20. The method according to claim 10, wherein the systemic sample is a whole blood sample, a serum sample, a plasma sample or a urine sample.

21. The method according to claim 10, wherein the muscle atrophy or muscle wasting condition is a muscle dystrophy; a central or spinal muscular atrophy;
    a neurogenic muscular atrophy; a congenital myopathy; or an 'idiopathic' muscle wasting condition.

22. The method according to claim 10, wherein the myostatin pathway inhibitor is a myostatin antagonist or an ActRII antagonist.

23. The method according to claim 22, wherein the myostatin antagonist is an anti-myostatin antibody, a myostatin decoy, a follistatin or a follistatin analogue.

24. The method according to claim 22, wherein the ActRII antagonist is an anti-ActRII antibody, an ActRII decoy or an inhibitor of effectors downstream of the ActRII.

25. A method for determining whether a subject having or suspected of having a muscle atrophy or a muscle wasting condition will respond to treatment with a myostatin pathway inhibitor, the method comprising:
    (a) measuring a level of myostatin in at least one muscle biopsy sample obtained from a treatment target muscle in the subject; and
    (b) selecting a subject wherein the level of myostatin in the at least one muscle biopsy sample is higher than myostatin levels in muscle biopsy samples from individuals with significant muscle atrophy and/or severe or advanced muscle wasting conditions, but below myostatin levels in muscle biopsy samples from healthy individuals; and
    (c) administering a myostatin pathway inhibitor to the subject of (b).

26. The method according to claim 25, wherein the myostatin is measured as protein or mRNA.

27. The method according to claim 25, wherein the myostatin is measured in a pro-peptide or mature protein form.

28. The method according to claim 25, wherein the at least one muscle biopsy sample has been obtained from a skeletal muscle.

29. The method according to claim 25, wherein the muscle atrophy or muscle wasting condition is a muscle dystrophy; a central or spinal muscular atrophy;
    a neurogenic muscular atrophy; a congenital myopathy; or an 'idiopathic' muscle wasting condition.

30. The method according to claim 25, wherein the myostatin pathway inhibitor is a myostatin antagonist or an ActRII antagonist.

31. The method according to claim 30, wherein the myostatin antagonist is an anti-myostatin antibody, a myostatin decoy, a follistatin or a follistatin analogue.

32. The method according to claim 30, wherein the ActRII antagonist is an anti-ActRII antibody, an ActRII decoy or an inhibitor of effectors downstream of the ActRII.

33. A method for determining whether a subject having or suspected of having a muscle atrophy or a muscle wasting condition will respond to treatment with a myostatin pathway inhibitor, the method comprising:
    (a) measuring a level of myostatin in at least one muscle biopsy obtained from a treatment target muscle in the subject; and
    (b) measuring a level of myostatin in a systemic sample obtained from the subject,
    (c) selecting a subject wherein:
        (i) the level of myostatin in the systemic sample is higher than myostatin levels in systemic samples from individuals with significant muscle atrophy and/or severe or advanced muscle wasting conditions, but below myostatin levels in systemic samples from healthy individuals; and
        (ii) the level of myostatin in the at least one muscle biopsy sample is higher than myostatin levels in muscle biopsy samples from individuals with significant muscle atrophy and/or severe or advanced muscle wasting conditions, but below myostatin levels in muscle biopsy samples from heathy individuals; and
(d) administering a myostatin pathway inhibitor to the subject of (c).

34. The method according to claim 33, wherein the myostatin is measured as protein or mRNA.

35. The method according to claim 33, wherein the myostatin is measured in a pro-peptide or mature protein form.

36. The method according to claim 33, wherein the at least one muscle biopsy sample has been obtained from a skeletal muscle.

37. The method according to claim 33, wherein the systemic sample is a whole blood sample, a serum sample, a plasma sample or a urine sample.

38. The method according to claim 33, wherein the muscle atrophy or muscle wasting condition is a muscle dystrophy; a central or spinal muscular atrophy; a neurogenic muscular atrophy; a congenital myopathy; or an 'idiopathic' muscle wasting condition.

39. The method according to claim 33, wherein the myostatin pathway inhibitor is a myostatin antagonist or an ActRII antagonist.

40. The method according to claim 39, wherein the myostatin antagonist is an anti-myostatin antibody, a myostatin decoy, a follistatin or a follistatin analogue.

41. The method according to claim 39, wherein the ActRII antagonist is an anti-ActRII antibody, an ActRII decoy or an inhibitor of effectors downstream of the ActRII.

42. A method for treating muscle atrophy or a muscle wasting condition, the method comprising:
(a) measuring a level of myostatin in at least one muscle biopsy obtained from a treatment target muscle in a subject having or suspected of having the muscle atrophy or the muscle wasting condition; and
(b) selecting a subject wherein the level of myostatin in the at least one muscle biopsy sample is higher than myostatin levels in muscle biopsy samples from individuals with significant muscle atrophy and/or severe or advanced muscle wasting conditions, but below myostatin levels in muscle biopsy samples from healthy individuals; and (c) administering a treatment for the muscle atrophy or the muscle wasting condition to the subject of (b).

43. The method according to claim 42, wherein the myostatin is measured as protein or mRNA.

44. The method according to claim 42, wherein the myostatin is measured in a pro-peptide or mature protein form.

45. The method according to claim 42, wherein the at least one muscle biopsy sample has been obtained from a skeletal muscle.

46. The method according to claim 42, wherein the systemic sample is a whole blood sample, a serum sample, a plasma sample or a urine sample.

47. The method according to claim 42, wherein the muscle atrophy or muscle wasting condition is a muscle dystrophy; a central or spinal muscular atrophy; a neurogenic muscular atrophy; a congenital myopathy; or an 'idiopathic' muscle wasting condition.

48. The method according to claim 42, wherein the myostatin pathway inhibitor is a myostatin antagonist or an ActRII antagonist.

49. The method according to claim 48, wherein the myostatin antagonist is an anti-myostatin antibody, a myostatin decoy, a follistatin or a follistatin analogue.

50. The method according to claim 48, wherein the ActRII antagonist is an anti-ActRII antibody, an ActRII decoy or an inhibitor of effectors downstream of the ActRII.

51. A method for treating muscle atrophy or a muscle wasting condition, the method comprising:
(a) measuring a level of myostatin in at least one muscle biopsy sample obtained from a treatment target muscle in a subject having or suspected of having the muscle atrophy or the muscle wasting condition; and
(b) measuring a level of myostatin in a systemic sample obtained from the subject;
(c) selecting a subject wherein:
(i) the level of myostatin in the systemic sample is higher than myostatin levels in systemic samples from individuals with significant muscle atrophy and/or severe or advanced muscle wasting conditions, but below myostatin levels in systemic samples from healthy individuals; and
(ii) the level of myostatin in the at least one muscle biopsy sample is higher than myostatin levels in muscle biopsy samples from individuals with significant muscle atrophy and/or severe or advanced muscle wasting conditions, but below myostatin levels in muscle biopsy samples from healthy individuals; and (d) administering a treatment for the muscle atrophy or the muscle wasting condition to the subject of (c).

52. The method according to claim 51, wherein the myostatin is measured as protein or mRNA.

53. The method according to claim 51, wherein the myostatin is measured in a pro-peptide or mature protein form.

54. The method according to claim 51, wherein the at least one muscle biopsy sample has been obtained from a skeletal muscle.

55. The method according to claim 51, wherein the systemic sample is a whole blood sample, a serum sample, a plasma sample or a urine sample.

56. The method according to claim 51, wherein the muscle atrophy or muscle wasting condition is a muscle dystrophy; a central or spinal muscular atrophy; a neurogenic muscular atrophy; a congenital myopathy; or an 'idiopathic' muscle wasting condition.

57. The method according to claim 51, wherein the myostatin pathway inhibitor is a myostatin antagonist or an ActRII antagonist.

58. The method according to claim 57, wherein the myostatin antagonist is an anti-myostatin antibody, a myostatin decoy, a follistatin or a follistatin analogue.

59. The method according to claim 57, wherein the ActRII antagonist is an anti-ActRII antibody, an ActRII decoy or an inhibitor of effectors downstream of the ActRII.

60. A method for determining inclusion of a subject, having or suspected of having muscle atrophy or a muscle wasting condition into a clinical trial for evaluation of a myostatin pathway inhibitor, the method comprising:
(a) measuring a level of myostatin in at least one muscle biopsy obtained from a treatment target muscle in the subject; and
(b) selecting a subject wherein the level of myostatin in the at least one muscle biopsy sample is higher than myostatin levels in muscle biopsy samples from individuals with significant muscle atrophy and/or severe or advanced muscle wasting conditions, but below myostatin levels in muscle biopsy samples from healthy individuals;and
(c) including the subject of (b) in the clinical trial;

(d) commencing the clinical trial; and
(e) administering the myostatin pathway inhibitor to the subject.

61. The method according to claim 60, wherein the myostatin is measured as protein or mRNA.

62. The method according to claim 60, wherein the myostatin is measured in a pro-peptide or mature protein form.

63. The method according to claim 60, wherein the at least one muscle biopsy sample has been obtained from a skeletal muscle.

64. The method according to claim 60, wherein the muscle atrophy or muscle wasting condition is a muscle dystrophy; a central or spinal muscular atrophy;
 a neurogenic muscular atrophy; a congenital myopathy; or an 'idiopathic' muscle wasting condition.

65. The method according to claim 60, wherein the myostatin pathway inhibitor is a myostatin antagonist or an ActRII antagonist.

66. The method according to claim 65, wherein the myostatin antagonist is an anti-myostatin antibody, a myostatin decoy, a follistatin or a follistatin analogue.

67. The method according to claim 65, wherein the ActRII antagonist is an anti-ActRII antibody, an ActRII decoy or an inhibitor of effectors downstream of the ActRII.

68. A method for determining inclusion of a subject, having or suspected of having muscle atrophy or a muscle wasting condition into a clinical trial for evaluation of a myostatin pathway inhibitor, the method comprising:
 (a) measuring a level of myostatin in at least one muscle biopsy obtained from a treatment target muscle in the subject; and
 (b) measuring a level of myostatin in a systemic sample obtained from the subject;
 (c) selecting a subject wherein:
  (i) the level of myostatin in the systemic sample is higher than myostatin levels in systemic samples from individuals with significant muscle atrophy and/or severe or advanced muscle wasting conditions, but below myostatin levels in systemic samples from healthy individuals; and
  (ii) the level of myostatin in the at least one muscle biopsy sample is higher than myostatin levels in muscle biopsy samples from individuals with significant muscle atrophy and/or severe or advanced muscle wasting conditions, but below myostatin levels in muscle biopshy samples from healthy individuals;
 (d) including the subject of (c) in the clinical trial;
 (e) commencing the clinical trial; and
 (f) administering the myostatin pathway inhibitor to the subject.

69. The method according to claim 68, wherein the myostatin is measured as protein or mRNA.

70. The method according to claim 68, wherein the myostatin is measured in a pro-peptide or mature protein form.

71. The method according to claim 68, wherein the at least one muscle biopsy sample has been obtained from a skeletal muscle.

72. The method according to claim 68, wherein the systemic sample is a whole blood sample, a serum sample, a plasma sample or a urine sample.

73. The method according to claim 68, wherein the muscle atrophy or muscle wasting condition is a muscle dystrophy; a central or spinal muscular atrophy;
 a neurogenic muscular atrophy; a congenital myopathy; or an 'idiopathic' muscle wasting condition.

74. The method according to claim 68, wherein the myostatin pathway inhibitor is a myostatin antagonist or an ActRII antagonist.

75. The method according to claim 74, wherein the myostatin antagonist is an anti-myostatin antibody, a myostatin decoy, a follistatin or a follistatin analogue.

76. The method according to claim 74, wherein the ActRII antagonist is an anti-ActRII antibody, an ActRII decoy or an inhibitor of effectors downstream of the ActRII.

* * * * *